United States Patent [19]

Nelson

[11] 4,048,194
[45] Sept. 13, 1977

[54] 6α-METHOXY-4α-HYDROXY-2β-HYDROX-YMETHYL-3α-TETRAHYDROPYRANA-CETIC ACID 4α γ-LACTONE ETHERS AND ACYLATES

[75] Inventor: Norman A. Nelson, Galesburg, Mich.

[73] Assignee: The Upjohn Company, Kalamazoo, Mich.

[21] Appl. No.: 676,893

[22] Filed: Apr. 14, 1976

[51] Int. Cl.$^2$ .......................................... C07D 493/04
[52] U.S. Cl. .............................. 260/343.6; 260/343; 260/343.3 R; 260/343.5; 260/345.7 P; 260/345.8 P; 260/347.3; 260/347.4; 260/405.5; 424/283; 542/427; 542/426
[58] Field of Search ..................................... 260/343.6

[56] References Cited
U.S. PATENT DOCUMENTS 3,971,826  7/1976  Hess et al. .......................... 260/520 B Primary Examiner—Cecilia M. S. Jaisle
Attorney, Agent, or Firm—Robert A. Armitage

[57] ABSTRACT

The present specification provides novel intermediates and novel processes for the synthesis of Thromboxane $B_2$ (11a-homo-11a-oxa-$PGF_{2\alpha}$), its 15-epimer, and various carboxyl derivatives thereof. In particular, there are disclosed various bicyclic tetrahydropyran containing lactones useful in the above processes, and corresponding acyclic lactones.

3 Claims, No Drawings

6α-METHOXY-4α-HYDROXY-2β-HYDROXYMETHYL-3α-TETRAHYDROPYRANACETIC ACID 4α γ-LACTONE ETHERS AND ACYLATES

BACKGROUND OF THE INVENTION

The present invention provides novel intermediates and chemical processes which are useful in the preparation of Thromboxane B$_2$ (TXB$_2$).

Thromboxane B$_2$ has the structure:

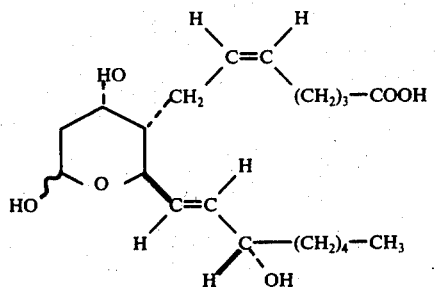

I and can be considered as a derivative of thromboxanoic acid or 11a-homo-11a-oxa-prostanoic acid which has the following structure and carbon atom numbering:

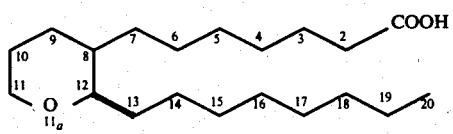

II

A systematic name for thromboxanoic acid is 7-[2β-octyl-tetrahydropyran-3α-yl]-heptanoic acid.

Alternatively Thromboxane B$_2$ is named as an analog of PGF$_{2\alpha}$, i.e., 11a-homo-11a-oxa-PGF$_{2\alpha}$.

In the above formulas, as well as in the formulas hereinafter given, broken line attachments to the tetrahydropyran ring indicate substituents in alpha configuration i.e., below the plane of the tetrahydropyran ring. Heavy solid line attachments to the tetrahydropyran ring indicate substituents in beta configuration, i.e., above the plane of the cyclopentane ring. The use of wavy lines (∼) herein will represent attachment of substituents in either the alpha or beta configuration or attachment in a mixture of alpha and beta configurations.

The side-chain hydroxy at C-15 in the above formulas is in S configuration. See, Nature 212, 38 (1966) for discussion of the stereochemistry of the prostaglandins, which discussion applies hereto with respect to TXB$_2$. Expressions such as C-15, and the like, refer to the carbon atom in Thromoxane B$_2$ which is in the position corresponding to the position of the same number in thromboxanoic acid.

Molecules of the known prostaglandins each have several centers of asymmetry, and can exist in racemic (optically inactive) form and in either of the two enantiomeric (optically active) forms, i.e. the dextrorotatory and levorotatory forms. Likewise TXB$_2$, which as discussed above is alternatively nominated as 11a-homo-11a-oxa-PGF$_{2\alpha}$, has similar centers of asymmetry, and thus, likewise can exist in optically active or racemic form. As drawn, the above formulas each represent the particular optically active form of the TXB$_2$ as is obtained biosynthetically, for example, as obtained by Samuelsson below. The mirror image of each of these formulas represents the other enantiomer of TXB$_2$. The racemic form of TXB$_2$ contains equal numbers of both enantiomeric molecules, and one of the above formulas and the mirror image of that formula is needed to represent correctly racemic TXB$_2$. For convenience hereinafter, use of the term, thromboxane or "TX" will mean the optically active form of that thromboxane thereby referred to with the same absolute configuration as TXB$_2$ obtained biosynthetically by Sameulsson. When reference to the racemic form of TXB$_2$ is intended, the word "racemic" or "dl" will precede the name, i.e. dl-TXB$_2$.

The term "thromboxane intermediate " as used herein, refers to any cyclopentane or tetrahydropyran derivative or acyclic compound which is useful in preparing TXB$_2$.

When a formula, as drawn herein, is used to depict a thromboxane intermediate each such formula represents the particular stereoisomer of the thromboxane intermediate which is useful in preparing TXB$_2$ of the same relative stereochemical configuration as TXB$_2$ obtained biosynthetically.

With respect to the asymmetric C-11 position of TXB$_2$, the hemiacetal structure about this carbon atom results in the presence of two diastereiomeric forms: the α-hydroxyl and β-hydroxy anomers. Due to the mutoratation resulting from the conversion of TXB$_2$ to its hydroxy-aldehyde form, e.g.

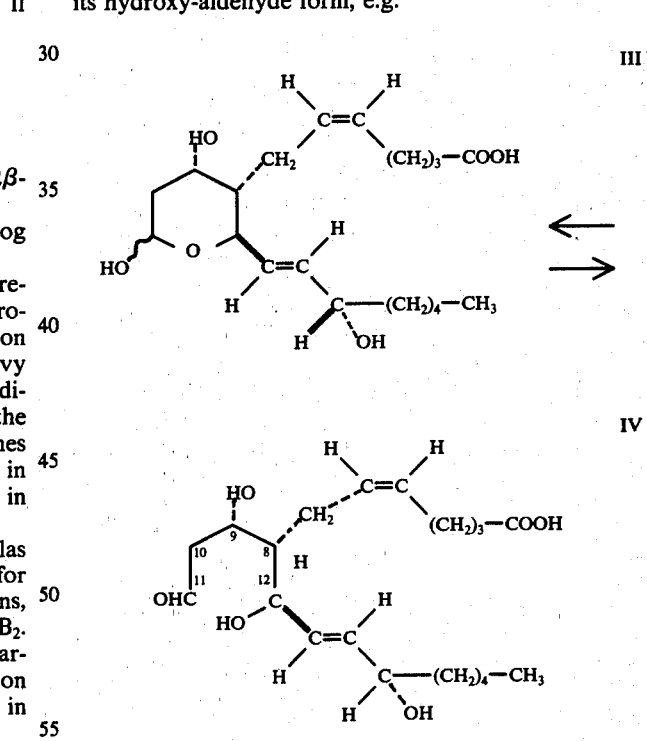

in, for example, aqueous and other solutions, the 11-hydroxyl represents an equilibrium mixture of alpha and beta hydroxy anomers, depicted by a ∼ OH, herein.

In formulas herein (e.g., formula IV) where a cyclopentane or tetrahydropyran ring is not present, such a ring having been cleaved or to be introduced in subsequent reaction steps, the convention by which substituents about asymmetric centers are depicted as alpha or beta is as defined above, but with respect to the plane of the various atoms which comprised said ring before its cleavage or will comprise said ring as synthesized in subsequent reaction steps. Thus, for example, in formula IV the oxygen atom of the 12-hydroxy substituent, having formerly been or successively to be the 11a-oxa of the tetrahydropyran ring is viewed as planar with C-8 to C-11 and C-12. Accordingly the C-12 side chain is beta to this plane and thus rendered by a heavy solid line, while the C-12 hydrogen is alpha to this plane and thus rendered by a dotted line.

Thromboxane $B_2$ is known in the art. This compound was prepared biosynthetically from arachadonic acid by B. Samuelsson, Proc. Nat. Acad. Sci. U.S.A. 71, 3400-3404 (1974). This compound alternately is named by him as 8-(1-hydroxy-3-oxopropyl)-9,12L-dehydroxy-5,10-heptadecadienoic acid, hemiacetal or PHD.

$TXB_2$ is produced biosynthetically from arachadonic acid, employing the cyclic oxygenase system which is responsible for the production of prostaglandins from arachadonic acid.

$TXB_2$, 15-epi-$TXB_2$, their esters and pharmacologically acceptable salts have been discovered to be extremely potent in causing various biological responses. For that reason, these compounds have been found to be useful for pharmacological purposes.

These biological responses include:

a. stimulating smooth muscle (as shown by tests on guinea pig ileum, rabbet duodenum, or gerbil colon); and more especially and particularly b. affecting the reproductive organs of mammals as labor inducers, abortifacients, cervical dilators, regulators of the estrus, and regulators of the menstrual cycle.

Because of these biological responses, these $TXB_2$ compounds are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

These $TXB_2$ compounds, being extremely potent in causing stimulation of smooth muscle, are also highly active in potentiating other known smooth muscle stimulators, for example, oxytocic agents, e.g., oxytocin, and the various ergot alkaloids including derivatives and analogs thereof. Therefore, these compounds for example, are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the $TXB_2$ compound is administered by intravenous infusion immediately after abortion of delivery at a dose in the range about 0.01 to about 50µg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The $TXB_2$ compounds, being useful in place of oxytocin to induce labor, are used in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 µg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The compounds are further useful for controlling the the reproductive cycle in mensturating female mammals, including humans. Menstruating female mammals are those mammals which are mature enough to menstruate, but not so old that regular menstruation has ceased. For that purpose the $TXB_2$ compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by thromboxanes is also useful in operative gynecology such as D and C (Cervical Dilation and Uterine Curettage) where mechanical dilation may cause performation of the uterus, cervical tears, or infections. It is also useful in diagnostic procedures where dilation is necessary for tissue examination. For these purposes, the $TXB_2$ compound is administered locally or systemically.

$TXB_2$, for example is administered orally or vaginally at doses of about 5 to 50 mg. per treatment of an adult female human, with from one to five treatments per 24 hour period. Alternatively $TXB_2$ is administered intramuscularly or subcutaneously at doses of about one to 25 mg. per treatment. The exact dosages for these purposes depend on the age, weight, and condition of the patient or animal.

These compounds are further useful in domestic animals as an abortifacient (especially for feedlot heifers), as an aid to estrus detection, and for regulation or synchronization of estrus. Domestic animals include horses, cattle, sheep, and swine. The regulation or synchronization of estrus allows for more efficient management of both conception and labor by enabling the herdsman to breed all his females in short pre-defined intervals. This synchronization results in a higher percentage of live births than the percentage achieved by natural control. The $TXB_2$ compound is injected or applied in a feed at doses of 0.1-100 mg. per animal and may be combined with other agents such as steriods. Dosing schedules will depend on the species treated. For example, mares are given the prostaglandin 5 to 8 days after ovulation and return to estrus. Cattle, are treated at regular intervals over a 3 week period to advantageously bring all into estrus at the same time.

SUMMARY OF THE INVENTION

The present invention provides novel intermediates and processes for the production of Thromboxane $B_2$, its 15-epimer, and various carboxyl derivatives thereof. In particular, there are disclosed herein novel processes in Charts A-F.

With respect to Chart A the transformation of the formula XXIV compound to the formula XXV or XXVIII compound and each sucessive transformation or series of transformations thereafter represents a novel element of the present disclosure. Likewise, in Chart B transformation of the formula XLII compound to the formula XLIII compound and each successive transformation or series of transformations thereafter represent a novel element of the present disclosure. Further, each of the transformations and series of transformations in Charts C and D represent novel elements of the present disclosure.

In addition to the processes depicted by the Charts herein, various intermediates of Charts A–D represent novel elements of the present disclosure. In particular, formulas XXV to XXXVa or XXXVb of Chart A, formulas XLIII–LII of Chart B, formulas LXII–LXIV of Chart C, and formulas LXXII–LXXV of Chart D represent novel elements of the present disclosure.

Finally, 15-epi-TXB$_2$ depicted by formula LXXVII and the various compounds of formula LXXVII wherein R$_1$ is not hydrogen represent novel derivatives or isomers of known TXB$_2$.

With respect to Charts E and F, the transformation of the formula XCI compound to the formula XCII compound and each successive transformation or series of transformations thereafter represents a novel element of the present disclosure.

In addition to the processes depicted by Charts E and F, various intermediates of Charts E and F represent novel elements of the present disclosure. In particular, formulas XCII–XCIV of Chart F represent novel elements of the novel disclosure.

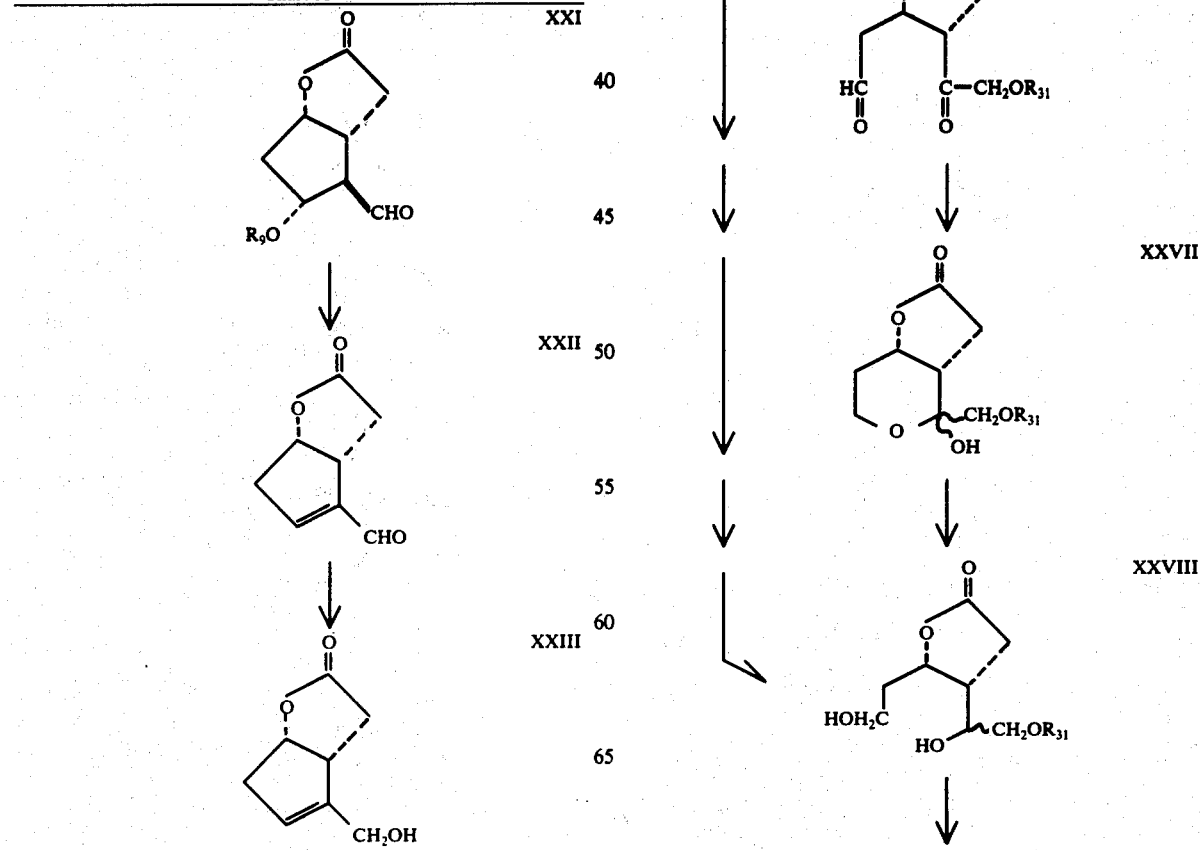

Chart A

-continued
Chart A

XXIX
XXX
XXXI
XXXII
XXXIV
XXXVa

-continued
Chart A

XXXVb

Chart B

XLI
XLII
XLIII
XLIV
XLV

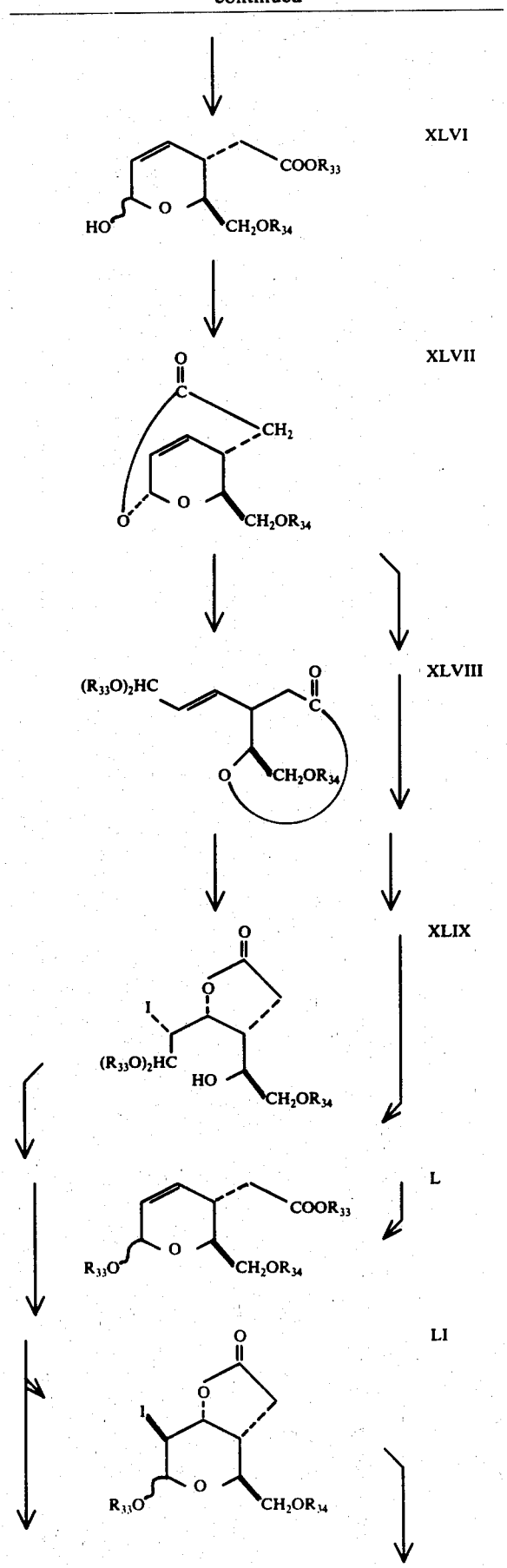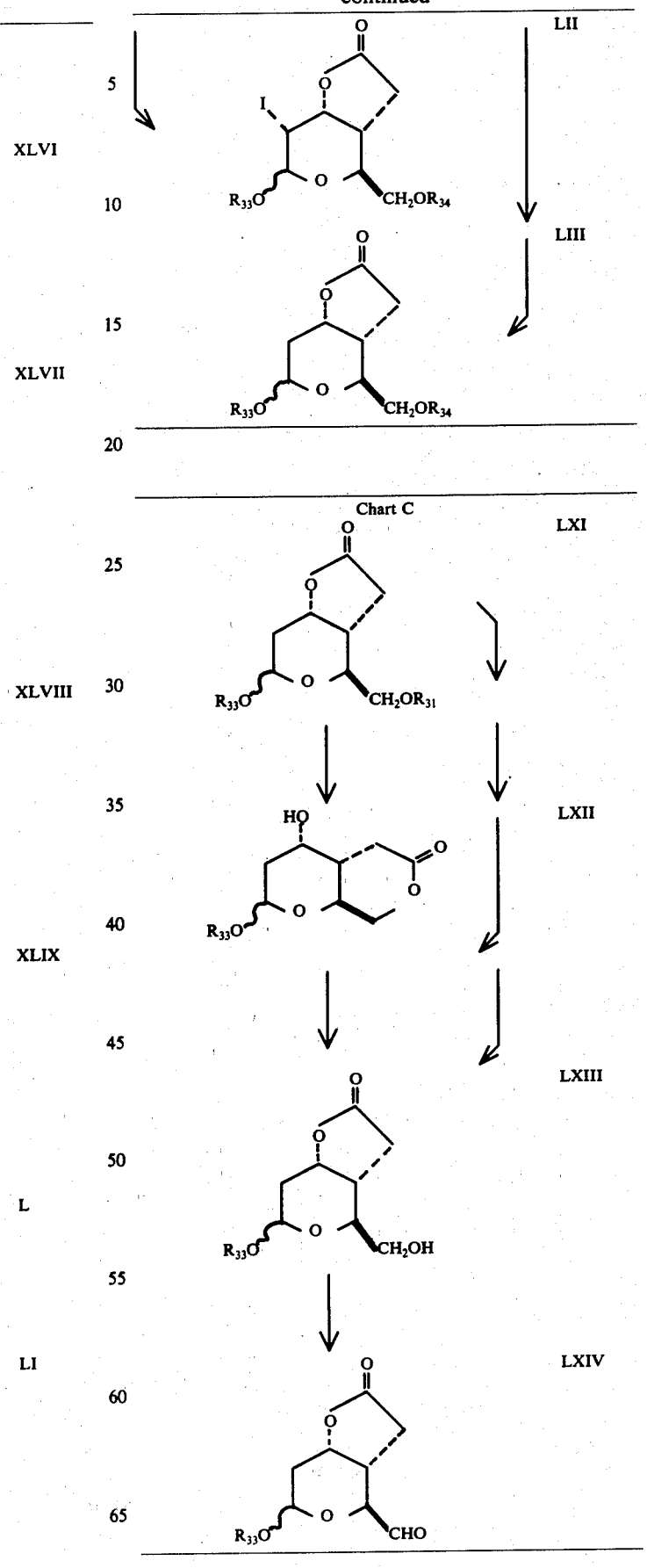

Chart D
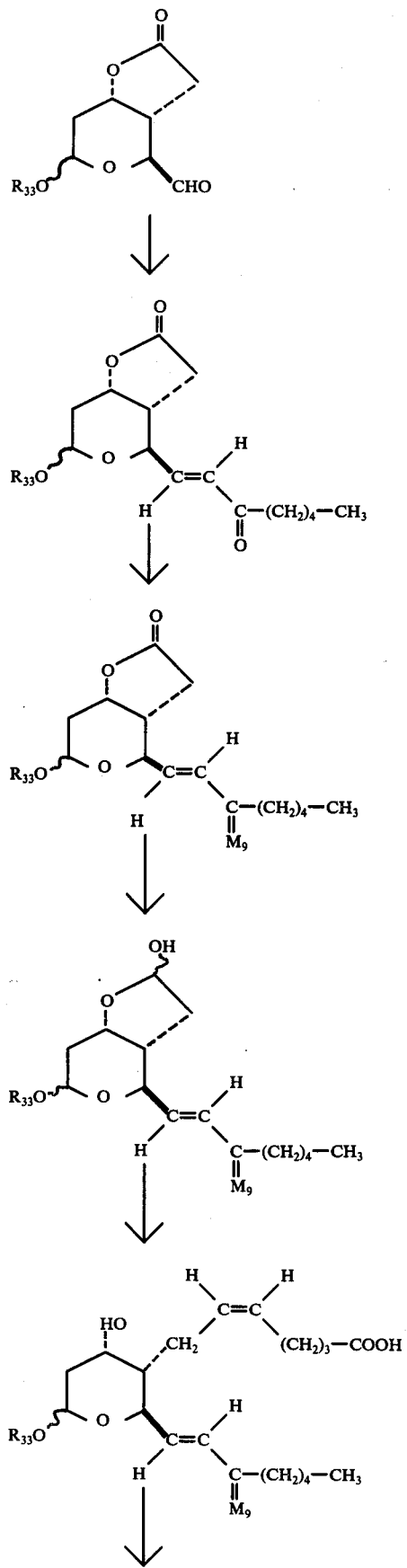
Chart D-continued
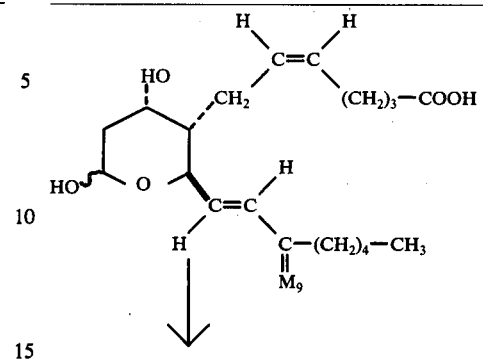
Chart E
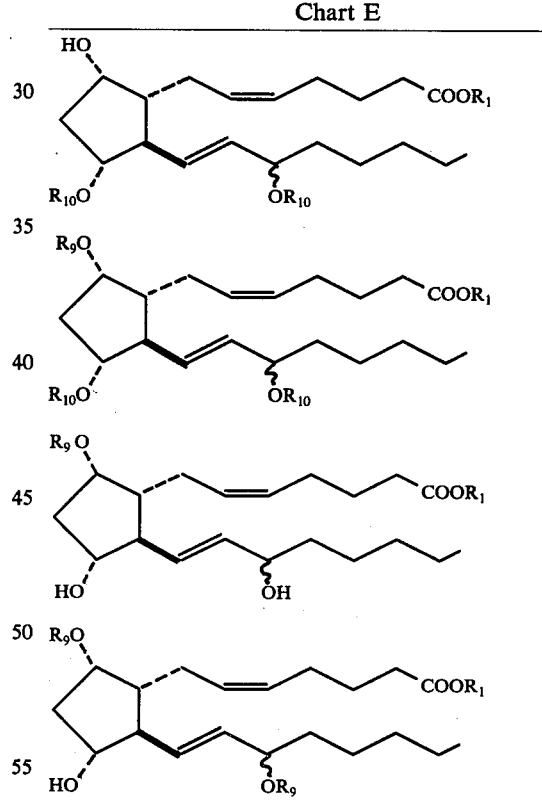
Chart F
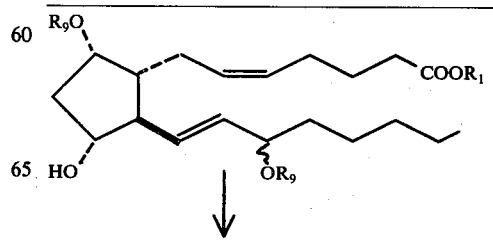

Chart F-continued

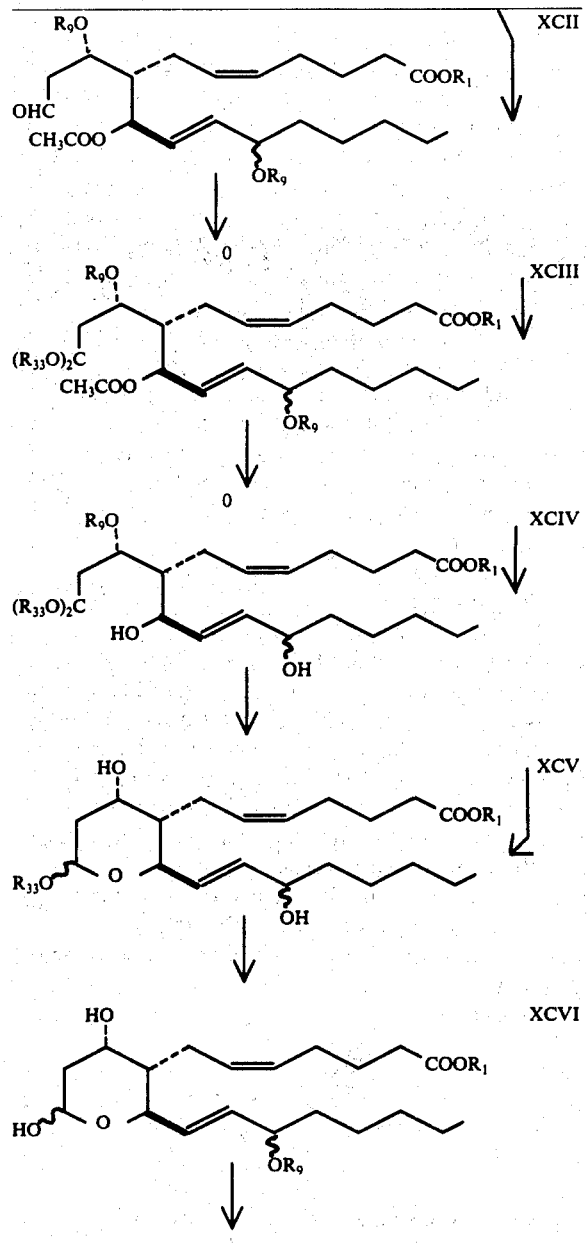

The following symbols, as used herein are defined as follows:

$M_9$ is

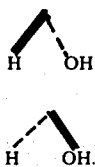

or

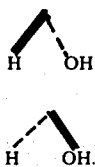

$R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation.

$R_9$ is an acyl protecting group. Acyl protecting groups according to $R_9$, include:

a. benzoyl;

b. benzoyl substituted with one to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;

c. benzoyl substituted with alkoxycarbonyl of 2 to 5 carbon atoms, inclusive;

d. naphthoyl;

e. naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and that the total number of carbon atoms in the substituents on either of the fused aromatic rings does not exceed 10 carbon atoms, with the further proviso that the various substituents are the same or different; or f. alkanoyl of 2 to 12 carbon atoms, inclusive.

In preparing these acyl derivative of a hydroxy-containing compound herein, methods generally known in the art are employed. Thus, for example, an aromatic acid of the formula $R_9OH$, wherein $R_9$ is as defined above (e.g., benzoic acid), is reacted with the hydroxy-containing compound in the presence of a dehydrating agent, e.g. sulfuric acid, zinc chloride, or p-toluenesulfonic acid; or alternatively an anhydride of the aromatic acid of the formula $(R_9)_2O$ (e.g., benzoic anhydride) is used.

Preferably, however, the process described in the above paragraph proceeds by use of the appropriate acyl halide, e.g., $R_9Hal$, wherein Hal is chloro, bromo, or iodo. For example, benzoyl chloride is reacted with the hydroxyl-containing compound in the presence of a hydrogen chloride scavenger, e.g. a tertiary amine such as pyridine, triethylamine or the like. The reaction is carried out under a variety of conditions, using procedures generally known in the art. Generally mild conditions are employed: 0°–60° C., contacting the reactants in a liquid medium (e.g., excess pyridine or an inert solvent such as benzene, toluene, o chloroform). The acylating agent is used either in stoichiometric amount or in substantial stoichiometric excess.

As examples of $R_9$, the following compounds are available as acids ($R_9OH$), anhydrides (($R_9)_2O$), or acyl chlorides ($R_3Cl$):- benzoyl; substituted benzoyl, e.g., 2-, 3-, or 4-)-methylbenzoyl, (2-, 3-, or 4-)-ethyl benzoyl, (2-, 3-, or 4-)-isopropylbenzoyl, (2-, 3-, or 4-)-tert-butyl benzoyl, 2,4-dimethylbenzoyl, 3,5-dimethylbenzoyl, 2-isopropyltoluyl, 2,4,6-trimethylbenzoyl, pentamethylbenzoyl, alphaphenyl-(2-, 3-, or 4-)-toluyl, (2-, 3-, or 4-)-phenethylbenzoyl, (2-, 3-, or 4-)-nitrobenzoyl, (2,4-, 2,5-, or 2,3-)-dinitrobenzoyl, 2,3-dimethyl-2-nitrobenzoyl, 4,5-dimethyl- 2-nitrobenzoyl, 2-nitro-6-phenethylbenzoyl, 3-nitro-2-phenethylbenzoyl, 2-nitro-6-phenethylbenzoyl, 3-nitro-2-phenethylbenzoyl; mono esterified phthaloyl, isophthaloyl, or terephthaloyl; 1- or 2-naphthoyl; substituted naphthoyl, e.g., (2-, 3-, 4-, 5-, 6-, or 7-)-methyl-1-naphthoyl, (2- or 4-) ethyl-1-naphthoyl, 2-isopropyl-1-naphthoyl, 4,5-dimethyl-1-naphthoyl, 6-isopropyl-4-methyl-1-naphthoyl, 8-benxyl-1-naphthoyl, (3-, 4-, 5-, or 8-)-nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl.

There may be employed, therefore, benzoyl chloride, 4-nitrobenzoyl chloride, 3,5-dinitrobenzoyl chloride, or the like, i.e. $R_9Cl$ compounds corresponding to the above $R_9$ groups. If the acyl chloride is not available, it is prepared from the corresponding acid and phosphorus pentachloride as is known in the art. It is preferred that the $R_9OH$, $(R_9)_2O$, or $R_9Cl$ reactant does not have bulky hindering substituents, e.g. tert-butyl on both of the ring carbon atoms adjacent to the carbonyl attaching cite.

The acyl protecting groups, according to $R_9$, are removed by deacylation. Alkali metal carbonate are employed effectively at ambient temperature for this purpose. For example, potassium carbonate in methanol at about 25° C. is advantageously employed.

$R_{10}$ is a blocking group which is herein defined to be any group which replaces a hydroxy hydrogen and is neither attacked nor is reactive to the reagents used in the transformations used herein as an hydroxy is and which is subsequently replaceable with hydrogen in the preparation herein of $TXB_2$. Several such blocking groups are known in the art, e.g. tetrahydropyranyl and substituted tetrahydropyranyl. See for reference E.J. corey, Proceedings of the Robert A. Welch Foundation Conference on Chemical Research, 12, Organic Synthesis, pgs. 51-79 (1969). Those blocking groups which have been found useful include
a. tetrahydropyranyl;
b. tetrahydrofuranyl; and
c. a group of the formula

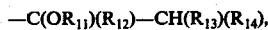

wherein $R_{11}$ is alkyl of one to 18 carbon atoms, inclusive, cycloalkyl of 3 to 10 carbon atoms, inclusive aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together —(CH$_2$)$_a$—or —(CH$_2$)$_b$—O—(CH$_2$)$_c$, wherein $a$ is 3, 4, or 5, or $b$ is one, 2, or 3, and $c$ is one, 2, or 3, with the proviso that $b$ plus $c$ is 2, 3, or 4, with the further proviso that $R_{12}$ and $R_{13}$ may be the same or different, and wherein $R_{14}$ is hydrogen or phenyl.

When the blocking group $R_{10}$ is tetrahydropyranyl, the tetrahydropyranyl ether derivative of any hydroxy moieties of the PG-type intermediates herein is obtained by reaction of the hydroxy-containing compound with 2,3-dihydropyran in an inert solvent, e.g. dichloromethane, in the presence of an acid condensing agent such as p-toluenesulfonic acid or pyridine hydrochloride. The dihydropyran is used in large stoichoimetric excess, preferably 4 to 10 times the stoichoimetric amount. The reaction is normally complete in less than an hour at 20° to 50° C.

When the blocking group is tetrahydrofuranyl, 2,3-dihydrofuran is used, as described in the preceding paragraph, in place of the 2,3-dihydropyran.

When the blocking group is of the formula

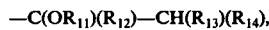

wherein $R_{11}$, $R_{12}$, $R_{13}$, and $R_{14}$ are as defined above, the appropriate reagent is a vinyl ether, e.g. isobutyl vinyl ether or any vinyl ether of the formula

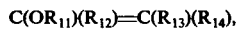

wherein $R_{11}$, $R_{12}$, $R_{13}$, and $R_{14}$ are as defined above; or an unsaturated cyclic or heterocyclic compound, e.g. 1-cyclohexen-1-yl methyl ether, or 5,6-dihydro-4-methoxy-2H-pyran. See C. B. Reese, et al., Journal of the Chemical Society 89, 3366 (1967). The reaction conditions for such vinyl ethers and unsaturated compounds are similar to those for dihydropyran above.

The blocking groups according to $R_{10}$ are removed by mild acidic hydrolysis. For example, by reaction with (1) hydrochloric acid in methanol; (2) a mixture of acetic acid, water, and tetrahydrofuran; or (3) aqueous citric acid or aqueous phosphoric acid in tetrahydrofuran, at temperatures below 55° C., hydrolysis of the blocking groups is achieved.

$R_{32}$ is —Si(G$_1$)$_3$, wherein G$_1$ is alkyl of one to 4 carbon atoms, aralkyl of 7 to 12 carbon atoms, phenyl, or phenyl substituted with one or 2 fluoro, chloro, or alkyl of one to 4 carbon atoms, with the proviso that in the —SI—(G$_1$)$_3$ moiety the various G$_1$'s are the same or different. Preferably $R_{32}$ is trimethylsilyl, or some other conveniently available, readily hydrolysable silyl group.

$R_{33}$ is alkyl of one to 5 carbon atoms, inclusive. Preferably $R_5$ is methyl or ethyl.

$R_{34}$ is an arylmethyl hydroxyhydrogen replacing group, which is defined as any arylmethyl group whicch replaces the hydroxy hydrogen of the intermediates in the preparation of $TXB_2$ herein which is subsequently replaceable by hydrogen in the processes herein for preparation of $TXB_2$, being stable with respect to the various reactions to which $R_{34}$-containing compounds are subjected and being introduced and subsequently hydrolysed by hydrogenolysis under conditions which yield to substantially quantitative yields of desired products (e.g., the primary alcohol).

Examples of arylmethyl hydroxy-hydrogen replacing groups are
a. benzyl (i.e.,

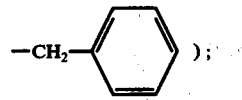

b. benzyl substituted by one to 5 alkyl of one to 4 carbon atoms, inclusive, chloro, bromo, iodo, fluoro, nitro, phenylalkyl of 7 to 12 carbon atoms, inclusive, with the further proviso that the various substituents are the same or different;
c. benzhydryl (i.e.,

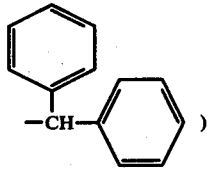

d. benzhydryl substituted by one to 10 alkyl of one to 4 carbon atoms, includive, chloro, bromo, iodo, fluoro, nitro, phenylalkyl of 7 to 12 carbon atoms, inclusive, with the further proviso that the various substituents are the same or different on each of the aromatic rings;
e. trityl (i.e.,

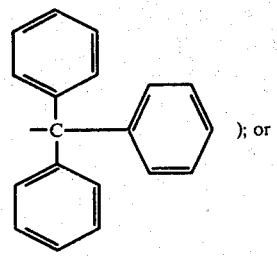); or f. trityl substituted by one to 15 alkyl of one to 4 carbon atoms, inclusive, chloro, bromo, iodo, fluoro, nitro, phenylalkyl of 7 to 12 carbon atoms, inclusive, with the further proviso that the various substituents are the same or different on each of the aromatic rings.

The introduction of such ether linkages to the hydroxy-containing compounds herein, particularly the benzyl or substituted benzyl ether proceeds by methods known in the art, for example by reaction of the hydroxy-containing compound with the benzyl or substituted benzyl halide (chloride or iodide) corresponding to the desired ether. This reaction proceeds in the presence of an appropriate condensing agent (e.g., silver oxide). The mixture is stirred and heated to 50°-80° C. Reaction times of four to 20 hours are ordinarily sufficient.

These arylmethyl groups are subsequently removed by hydrogenolysis, for example by catalytic hydrogenation over a 5-10% palladium-on-carbon catalyst.

$R_{31}$ is a hydroxy hydrogen replacing group which is stable to the reagents employed herein in the preparation of $TXB_2$, and subsequently, readily hydrolyzedor-hydrogenolysed as required herein. Those hydroxy-hydrogen replacing groups useful for this purpose include any acyl protecting group according to $R_9$, blocking group according to $R_{10}$, or arylmethyl hydroxy-hydrogen replacing group according to $R_{34}$.

With respect to Chart A, a method is provided whereby the formula XXI compound, known in the art in optically active form or as a mixture of isomers is transformed to either of the formula XXXV intermediates, which are useful according to processes to Charts C and D for preparing the $TXB_2$-type compounds of formula LXVII.

With respect to Chart A, the formula XXII compound is known. See, for example, Yankee, et al., Journal of the American Chemical Society 96, 5865 (1974). The formula XXII compound is otherwise available by methods known in the art.

The transformation of the formula XXI compound to the formula XXII compound proceeds by methods known in the art. For example, the formula XXI compound is dissolved in a suitable organic solvent (ethyl acetate, tetrahydrofuran, benzene, methylene chloride, chloroform, and the like), and thereafter treated with a weak base. For this purpose a base such as Florisil or various tertiary amines, e.g., triethylamine, are conveniently employed. The reaction proceeds at or about room temperature and is ordinarily complete within about 6 to 24 hr. Pure formula XXII product is then obtained by any suitable conventional procedure. For example, filtration or solvent extractions are employed, or alternatively and preferably column chromatography on Florisil employing ethyl acetate as a eluant provides a convenient method of recovering pure product.

Thereafter the formula XXII compound thus obtained is selectively reduced to the formula XXIII primary alcohol using reducing agents known to provide selective reduction of aldehydes in the presence of lactones. For this purpose, lithium tri-t-butoxyaluminum hydride in tetrahydrofuran is conveniently employed. Other reducing agents, for example, sodium, potassium, zinc, or lithiumborohydride in various alkanol solvents are further employed. The formula XXIII compound is then transformed to the formula XXIV compound by replacing the hydroxy hydrogen with an acyl protecting group, a blocking group, or an aryl methyl hydroxy hydrogen replacing group. For the introduction of any of these groups in the formula XXIII compound, methods described hereinabove for such a transformation are employed.

the formula XXIV compound is then transformed directly to the formula XXVIII compound by ozonolysis and reduction or alternatively transformed to the formula XXVIII compound by transformation successively to the formula XXV, XXVI, and XXVII compounds.

The transformation of the formula XXIV compound to the formula XXV compound proceeds by glycolization. Glycolization proceeds by methods known in the art. Thus, for this purpose osmium tetroxide is employed catalytically while N-methylmorpholine N-oxide is employed in slight stoichiometric excess. The mixture of these reactants is maintained with stirring at about 0°-50° C., but for convenience is preferably run at about abmient temperature. The reaction is ordinarily complete within about one to 3 hr. and the formula XXV glycol is then isolated by conventional means. For example, solvent extraction is employed or chromatographi purification and/or crystallization techniques are used.

In place of N-methylmorpholine,N-oxide, there are for example used other known oxidants such as potassium chlorate, hydrogen peroxide, and the like.

The formula XXV compound is oxidatively cleaved to the formula XXVI compound employing concentrated aqueous periodic acid ($H_5IO_6$) in the presence of an amine base (e.g. pyridine). About one and one-half molecular equivalents of the periodic acid and amine base are conveniently employed per equivalent of formul XXV starting material. The reaction is run at about -5° to 30° C. preferably at or about 0° C. The reaction proceeds by vigorous stirring and ordinarily is complete within about 2 to 20 min. The reaction mixture is then diluted with ethyl acetate and product recovered by filtration from the filtrate. Since the formula XXVI compound is relatively unstable, particularly in acidic or especially basic environments, it is ordinarily used without further purification in preparation of the formula XXVII and formula XXVIII compounds.

Alternatively, in place of periodic acid other reagents known to cleave glycol linkages, such as sodium periodate, manganese dioxide and lead tetraacetate are employed.

The formula XXVI compound is reduced to the formula XXVII and thereafter the formula XXVIII compound. This reduction is achieved employing reducing agents described above for the transformation of the formula XXII compound to the formula XXIII compound. In particular, sodium borohydride is particularly useful reagent for this purpose thus, the formula XXVI compound in a solvent (e.g. methanol:methylene chloride, 7:3) is treated with excess sodium borohydride with stirring at about 0° C. for between 10 min. and one hr.

Where recovery of the formula XXVII compound is desired the course of the reaction is followed by silica gel chromatography and when reduction of the formul XXVI compound to the formula XXVII compound is complete the reaction conditions are terminated by cautious destruction of the reducing agent, for example, by addition of acetic acid. The formula XXVII compound is then concentrated and isolated by conventional means as described above. This formula XXVII compound is then useful in the preparation of the formula XXVII compound or if the reaction conditions are maintained the formula XXVI compound is ultimately reduced directly to the formula XXVIII compound. This compound is obtained as an (1'RS) epimeric mixture which is separated into pure (1'R) or (1'S) isomers.

In identifying the stereochemistry about the asymmetric centers of the formula XXVIII compound (and likewise the corresponding formula XXIX, XXX, and XXI compounds) the convention described hereinabove is employed. Thus, for example, in each case the 5 carbon atoms which formerly comprised the cyclopentane ring and oxygen of the secondary hydroxyl are depicted as planar, since these are the latent tetrahydrofuran ring atoms of formula XXII. Accordingly, various substituents of asymmetric carbon atoms are depicted as either alpha or beta, or mixture thereof, to this plane.

However, in naming each of the formula XXVIII--XXXI compounds (and like acyclic compounds in successive charts), "R" and "S" nomenclature about asymmetric centers is employed. See R. S. Cahn, J. Chem. Ed., 41; 116-125 (1964).

Accordingly, the isomer of the formula XXVIII compound which leads to the formula XXXIV 2$\beta$-compound is of the "S" configuration at the asymmetric carbon atom containing the secondary hydroxyl. The formula XXVIII compound is then transformed to the formula XXX compound by silylation. Methods and reagents generally known in the art are employed. For discussion of the various silylating agents employed herein see Post, Silicones and Other Organic Silicon Compounds, Reinhold Publishing Co., New York, New York (1949). For procedures in effecting the instant silylation see Pierce, Silylation of Organic Compounds, Pierce Chemical Co., Rockford, Ill. (1968).

Since no speciaL stability requirements are demanded of the silyl containing intermediates herein, readily available silylating agents are preferably employed. For example, the silylation herein proceeds by treating the formula XXVIII compound, dissolved in a suitable organic solvent, such as tetrahydrofuran, with trimethylsilyl chloride and hexamethyldisilane. This reaction is run for convenience at or near ambient temperature and is ordinarily complete within about 15 to 20 hr. The course of the reaction is conveniently monitored by silica gel thin layer chromatography using for example ethyl acetate in hexane. In the preparation of the formula XXVIII compound the reaction proceeds first by the partial silylation of the hydroxyl in the position $\epsilon$ to the lactonized carboxyl (formula XXIX) and thereafter to the formula XXX product. Since in the employment of the process herein, recovery of the formula XXIX partially silylated product is not required, ordinarily, silylation of the formula XXVIII compound is allowed to proceed to completion.

The formula XXXI compound is prepared from the formula XXX compound by a selective oxidation of the silyl ether at the carbon atom $\epsilon$ to the lactonized carboxyl to the corresponding aldehyde. For this purpose, the Collins reagent is employed by methods known in the art. See R. Ratcliffe, et al., Journal of Organic Chemistry 35, 4000 (1970). For this purpose about 8 to 9 equivalents of oxidizing reagent are employed for each equivalent of formula XXX compound. The reaction is run at room temperature and is ordinarily complete in about 15 to 45 min. The product is then recovered by filtration of crude product through a mixture of Celite and acid-washed silica gel (1:2). The filtrate and diethyl ether washings are then combined, washed and concentrated to yield the formula XXI aldehyde.

This formula XXXI aldehyde is then transformed to the formula XXXII hemiacetal by desilylation, followed by hemiacetal formation. Thus, the formula XXXI product is dissolved in methanol or an aqueous methanol mixture sufficient to yield a homogeneous reaction mixture and allowed to react at 0° to 50° C. for about 1-5 hr. Preferably, however, reaction temperatures of between 20° and 40° C. are employed. Thereupon, the formula XXXII compound is isolated, by solvent extraction or silica gel chromatography, employing conventional methods.

The formula XXXIV compound is then prepared from the formula XXXII compound (when $R_{31}$ is not a blocking group according to $R_{10}$) by reaction of the formula XXXII compound with hydrogen chloride in an alkano corresponding to the alkyl group to be introduced into formula XXXII. The reaction proceeds at temperatures of about 0°-40° C., although it is preferred for convenience to allow the reaction to proceed at ambient temperature. The reaction is ordinarily complete within one to 24 hr. and thereafter the reaction mixture is diluted with excess organic solvent (e.g. ethyl acetate, diethyl ether, and methylene chloride). Thereafter pure formula XXXIV product is recovered by conventional means. For example, crude reaction mixture may be washed with basic brine and brine and thereafter chromatographed on silica gel. There are thereby recovered two isomeric alkyl acetals depicted by formula XXXIV.

When $R_{31}$ in the reaction sequence of Chart A is a blocking group according to $R_{10}$, then the procedure described above for the introduction of the alkyl group on the formula XXXII compound yields a hydrolyzed 2$\beta$-hydroxymethyl compound according to formula LXIII of Chart C.

Further, when $R_{31}$ is not a blocking group according to $R_{10}$, then the reaction described for the transformation of the formula XXXII compound to the formula XXXIV compound is optionally and preferably employed on the formula XXXI compound. Accordingly, by this optional method the formula XXXI compound is transformed directly to the formula XXXIV compound.

Thereafter, the formula XXV compounds are prepared by separation of diastereomerica mixtures of the formula XXXIV compound. For example, suitable conventional techniques for such a separation include silica gel chromatography.

Chart B provides an alternate method for the preparation of one species of the formula XXXIV compound (i.e., wherein $R_{31}$ is an arylmethyl hydroxy hydrogen replacing group according to $R_{34}$) from the formula XLI compound.

The formula XLI compound is known in the art or prepared by methods known in the art. This compound is transformed to the formula XLII compound by oxidation. Acidic oxidation reagents know in the art are employed in this transformation. For example, a Jones oxidation or Moffatt is employed. Reaction temperatures of between $-10°$ and $-10°$ C. are employed. Preferably, however, temperatures of $0°$ C. are used. This reaction is ordinarily complete within several minutes to several hr. and the formula XLII compound so produced is preferably transformed directly to the formula XLIII compound without chromatographic purification after normal extractive separation.

Accordingly, crude formula XLII compound is transformed to the formula XLIII dilactone by methods known in the art for the oxidation of ketones to lactones. Accordingly, a Baeyer-Villiger oxidation is employed. Accordingly, this oxidation proceeds by the use of any one of a number of peracids. For convenience, it is preferred to use peracids which are commercially avialable, such as perphthallic, peracetic, or m-chloroperbenzoic acid. The reaction can be conveniently carried out at ambient temperature, in which case the oxidation is ordinarily complete within 2-5 days. Thereafter, the formula XLIII compound is isomerized to the formula XLIV unsaturated lactone, This isomerization proceeds under basic conditions. For example, preferred bases are tertiary amines, and particularly convenient and useful tertiary amine for this purpose is 1,5-diazobicyclo[5.4.0]undec-5-ene (DBU). The formula XLIV compound is acidified, and then recovered by conventional means, e.g., solvent extraction. The formula XLIV compound is then transformed to the formula XLV compound by reduction of the formula XLIV lactone to a lactol. This reduction proceeds by conventional methods for such reductions, for example, the use of diisobutylaluminum hydride at or about -70° C. Other reducing, agents useful for this purpose, are alternately employed. For example, lithium-tri-tert-butoxy aluminum hydride or sodium bis-(2-methoxyethoxy)aluminum hydride are optionally employed.

The formula XLV lactol is then transformed to the formula XLVI methyl ester by alkyl esterification. Methods know in the art for the transformation of carboxylic free acids to corresponding alkyl esters, particularly and especially the use of the appropriate diazoalkane in a solvent such as diethyl ether, are employed. The formula XLVI compound is thereafter recovered in crude form by concentration under reduced pressure. The residue so obtained thereafter spontaneously lactonizes to formula XLVII compound, However, for the succeeding steps herein either the formula XLVII lactone is employed as depicted (i.e., transformation to either the formula XLVIII or formula L compound) or its formula XLVI methyl ester precursor is employed. In any event, either the formula XLVI or formula XLVII compound is transformed to the formula XLVIII and formula L compounds by treatment with a dry alkanol, corresponding to the $R_{33}$ alkyl group to be introduced in the formula XLVII compound and a catalytic amount of acid. For this purpose, hydrogen chloride gas in dry diethyl ether or a Lewis acid, such as boron trifluoride etherate are employed. Additionally, a trialkyl orthoalkanoate corresponding to the $R_{33}$ alkyl group to be introduced is added to the reaction mixture in a quantity sufficient to prevent any water present from interfering with the reaction. This reaction is preferably run for convenience at about ambient temperature and is ordinarily complete within several hours. The formula XLVIII and formula L compounds thereby produced are then recovered and separated by conventional means, e.g. chromatographic methods.

Thereafter, the formula XLVIII compound is converted to the formula XLIX iodo lactone by methods known in the art for this purpose. For example, the formula XLVIII lactone is treated with base (e.g., sodium hydroxide, followed by treatment with solid carbon dioxide, potassium iodide, and molecular iodine). The formula XLIX dialkyl acetal is then converted to the formula LI lactone methyl acetal by refluxing in a solution of benzene containing a catalytic amount of a condensing agent, such as p-toluenesulfonic acid.

Alternatively, the formula L compound product from the formula XLVIII compound is transformed to the formula LI compound by the iodo lactonization method described above in the preparation of the formula LXIX compound from the formula LXVIII compound.

Thereafter, the formula LI or LII compound in either of its diastereomeric forms (i.e., $6\alpha$-alkoxy, $6\beta$-alkoxy, $5\alpha$-iodo or $5\beta$-iodo) is transformed to the formula LIII compound by deiodination. A particularly convenient method for achieving this deiodination employs the method of Corey, et al., Journal of Organic Chemistry 40, 2554 (1975). Thus, by this method the formula LI or LII compound, tri-n-butylchloride, and sodium borohydride, are combined while irradiating with a tungsten Lamp.

Chart C provides a method whereby the formula LXI compound, as prepared in Charts A or B is transformed to the formula LXIV bicyclic lactone acetal aldehyde.

The formula LXI compound is transformed to the formula LXII compound when $R_3$, is an acyl protecting group, or the LXIII compound by hydrolysis or hydrogenolysis of the $R_{31}$ group. When $R_{31}$ is an acyl protecting group according to $R_9$, methods described above, e.g. the use of sodium methoxide, are employed. When $R_{31}$ is a blocking group according to $R_{10}$, hydrolysis proceeds by methods described hereinabove for removing blocking groups according to $R_{10}$, or alternatively the reaction conditions described for the transformation of the formula XXXI to formula XXXII compound are employed. Finally, when $R_{31}$ is an aryl methyl hydroxy hydrogen replacing group according to $R_{34}$, the transformation proceeds by hydrogenolysis. For this purpose, for example, as described above a palladium-on-catalyst is employed.

As indicated above, hydrolysis of the acyl protecting group results in a mixture of the formula LXII $\delta$-lactone and the formula LXIII $\gamma$-lactone. This formula LXII $\delta$-lactone can be recyclized to the formula LXIII lactone by treatment with sodium methoxide, followed by neutralization.

The formula LXIII alcohol is then oxidized to the corresponding aldehyde by oxidation. For this purpose the Collins oxidation (see R. Ratcliff, Journal of Organic Chemistry, 35, 4000 (1970); E. W. Yankee, et al., Journal of the American Chemical Society 96, 5865 (1974)); or Moffatt oxidation, (see Journal of the American Chemical Society, 85, 3027 (1963) or Journal of the American Chemical Society 87, 5661, 5670 (1965)), is employed.

Chart D provides a method whereby the formula LXXI bicyclic lactone acetal aldehyde, prepared according to Chart C, is transformed to Thromboxane $B_2$, its 15-epimer, or carboxyl derivatives thereof. The procedure described in Chart D is analogous to procedures known in the art for the preparation of $PGF_{2\alpha}$, its 15- epimer, or carboxyl derivatives thereof from the formula XXI compound of Chart A. See Corey, et al., Journal of the American Chemical Society 91, 5675–5677 (1969), particularly the transformation of the formula 8 compound to the formula 14 compound.

The formula LXXII compound is prepared from the formula LXXI compound employing a Wittig alkylation. Reagents known in the art are employed. The trans-enone lactone acetal is obtained stereospecifically. See for reference D. H. Wadsworth, Journal of Organic Chemistry 30, 680 (1965). In the preparation of the formula LXXII compound, certain phosphonates are employed in the Wittig reaction. These phosphonates are of the general formula $(R_{15}O)_2$ wherein $R_{15}$ is alkyl of one to 8 carbon atoms, inclusive. Phosphonates of the above general formula are prepared by methods known in the art. See Wadsworth, et al., as cited above.

The formula LXXII 3-oxo-bicyclic lactone acetal is transformed to a corresponding $3\alpha$- or $3\beta$-hydroxy compound by reduction of the 3-oxo moiety, followed by separation of $3\alpha$- and $3\beta$-epimers. For this reduction the known ketonic carbonyl reducing agents which do not reduce ester or acid groups or carbon carbon double bonds are employed. Examples of these reagents particularly useful for the present purposes are the metal borohydrides, especially sodium, potassium, and zinc borohydride. For the production of C-15 epimerically pure compounds, separation proceeds by methods known in the art. For example, silica gel chromatography is employed.

The formula LXXIII compound is then reduced to the formula LXXIV bicyclic lactol acetal by employing methods described above herein for reduction of lactones to lactols. Thus, diisobutylaluminum hydride is about −78° C. is advantageously employed herein.

Thereafter the formula LXXV compound is prepared from the formula LXXIV compound employing a Wittig alkylation with 4-carboxybutyltriphenylphosphonium bromide. The reaction proceeds as is generally known in the art, by first mixing 4-carboxybutyltriphenylphosphonium bromide with sodio dimethylsulfinylcarbanide, at ambient temperature, and thereafter adding the formula LXXIV bicyclic lactone acetal to this mixture.

The formula LXXV compound is then employed in the preparation of the formula LXXVI compound, Thromboxane $B_2$, by hydrolysis of the alkyl ether. For this purpose, mineral or organic acids, such as phosphoric acid, hydrochloric acid or trifluoroacetic acid are employed. Suitable reaction diluents are those which yield homogeneous reaction mixtures, for example, mixtures of water and tetrahydrofuran. The formula LXXVI product is then isolated and purified by conventional means. For example, solvent extraction is employed and thereafter purification by silica gel chromatography is used.

Thereafter, the carboxy hydrogen of the formula LXXVI compound is transformed to an $R_1$ moiety of the formula LXXVII compound by methods and procedures hereinbelow described. Accordingly, there is prepared the formula LXXVII compound: Thromboxane $B_2$ or its 15-epimer, or carboxyl derivatives thereof.

With respect to Chart E, a method is provided whereby the formula LXXXI $PGF_{2\alpha}$, 11,15-bis-ether, and carboxyl derivatives thereof are transformed to the formula LXXIV compound: a $PGF_{2\alpha}$, 9,15-diacylate, or carboxyl derivatives thereof. With respect to Chart E, the various reaction steps are known in the art.

The formula LXXXI compound is acylated, preparing the formula LXXXII compound according to procedures hereinabove described. Thus, methods described above for the introduction of acyl protecting groups according to $R_9$ are employed. Thereafter, the formula LXXXII compound is transformed to the formula LXXXIII compound by selective hydrolysis of the $R_{10}$ blocking groups in the presence of the acyl protecting group according to $R_9$. For this purpose, methods described above for the hydrolysis of $R_{10}$ blocking groups are employed. Accordingly, a mixture of acetic acid, water, and tetrahydrofuran is useful in this transformation.

The formula LXXXIII compound is then selectively acylated at the C-15 position, preparing the formula LXXXIV compound. This selective acylation proceeds by reacting one equivalent of acylating agent (e.g., the acyl anhydride) with the formula LXXXIII compound at low temperature. Preferably, the reaction is run at or below 0° C. Acylation is ordinarily complete within 1 to 3 hr. and formula LXXXIV product is recovered by conventional means from the mixture of 9,11- and 9,15-acylated products. Conventional separation techniques, e.g. chromatographic techniques, are employed.

Chart F provides a method whereby Thromboxane $B_2$, its 15-epimer, or carboxyl derivatives thereof are prepared from the formula XCI compound (as prepared in Chart E).

The formula XCI compound is transformed to the formula XCII aldehyde by reaction with lead-tetraacetate in benzene. The reaction proceeds rapidly at temperatures of about 40° to 60° C., and is ordinarily complete within about 45 min. to 2 hr. The resulting formula XCII product is unstable (e.g. subject to loss of $R_9OH$) and is accordingly converted to the formula XCIII acetal without further purification.

The preparation of the formula XCIII dialkyl acetal proceeds by methods described herinabove for the preparation of acetals from aldehydes, e.g. reaction with an alkanol in the presence of a trialkyl orthoalkanoate and catalytic amount of an acid. Thus, when $R_{33}$ is methyl, the present reaction proceeds by treatment of the formula XCII compound with methanol, methylorthoformate, and pyridine hydrochloride. Pure formula XCIII product is thereafter isolated by conventional methods, such as chromatography.

The formula XCIV compound is then prepared from the formula XCIII compound by removal of the acyl protecting groups. Methods described hereinabove are employed. Accordingly, sodium methoxide in methanol is employed in stoichiometric amounts, yielding the formula XCIV trihydroxy acetal. Optionally, the use of aqueous methanolic sodium hydroxide removes both the acyl protecting groups and $R_1$ ester.

The formula XCV compound is then prepared from the formula XCIV compound by hydrolysis of the acetal group. Methods described above for the hydrolysis of tetrahydropyranyl ethers (ie. acetic acid, water, and tetrahydrofuran mixtures) yield the formula XCIV product. More vigorous conditions of hydrolysis of the formula XCIV compound yield the formula XCVI product directly.

Optionally, however, the formula XCV compound is prepared directly from the formula XCII compound by treatment of the formula XCII compound with an alkanol and anhydrous mineral acid in diethyl ether. When $R_{33}$ is methyl, for example, methanol and ethereal 2N hydrochloric acid yield the formula XCV compound directly from the formula XCII product.

In the reaction sequence described by Charts E and F, the use of C-1 esters, particularly and especially lower alkyl esters, is preferred.

Diastereomeric mixtures, other than anomeric mixtures, when produced by any reaction step herein, are separated immediately by isolation and conventional separation techniques, e.g., chromatography. However, when isolation of any intermediate, which is produced as a non-anomeric diastereomeric mixture, is not required, then optionally the separation of such mixture is deferred to succeeding reactions, or if such a separation is not required due to a subsequent removal of centers of assymmetry (e.g., transformation of XXV to XXVI) or preparation of anomeric products (e.g., transformation of LXXV to LXXVI), then it is deleted entirely.

Optically active Thromboxane $B_2$ and related products are obtained from optically active intermediates, according to the process steps of the above charts. Likewise racemic $TXB_2$ compounds are obtained from corresponding racemic $TXB_2$ intermediates following the procedures in the above charts, e.g. when racemic intermediates are used in the reactions above, racemic products are obtained. These products may be used in their racemic form or if preferred they may be resolved as optically active enantiomers following procedures known in the art. For example, when a $TXB_2$ free acid is obtained, the racemic form thereof is resolved into $d$ and $l$ forms by reacting said free acid by known procedures with an optically active base (e.g., brucine or strychnine) thereby yielding a mixture of 2 diastereomers which are separable by procedures known in the art (fractional crystallization to yield the separate diastereomeric salts). The optically active acid may then be prepared from the salt by general procedures known to the art.

In all of the above described reactions, the products are separated by conventional means from starting material and impurities. For example, by use of silica gel chromatography monitored by thin layer chromatography the products of the various steps of the above charts are separated from the corresponding starting materials and impurities.

As discussed above, the processes herein described lead variously to acids ($R_1$ is hydrogen) or to esters.

When the alkyl ester has been obtained and an acid is desired, saponification procedures, as known in the art for PGF-type compounds are employed. Optionally, however, free acids are prepared by enzymatic process for transformation of PGE-type esters to their acid forms. Thus the $TXB_2$ methyl ester is combined with prepared enzyme powder and hydrolyzed. See for reference E. G. Daniels, Process for Producing An Esterase, U.S. Pat. No. 3,761,356.

When an acid has been prepared and an alkyl, cycloalkyl, or aralkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively. Similarly, diazocyclohexane and phenyldiazomethane yield cyclohexyl and benzyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for alkyl, cycloalkyl or aralkyl esterification of the carboxy moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, cyclopropyl iodide, cyclopentyl iodide, benzyl iodide, phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

Various methods are available for preparing phenyl or substituted phenyl esters within the scope of the invention from corresponding aromatic alcohols and the free acid TXB-type compounds, differing as to yield and purity of product.

Thus by one method, the TXB-type compound is converted to a tertiary amine salt, reacted with pivaloyl halide to give the mixed acid anhydride and then reacted with the aromatic alcohol. Alternatively, instead of pivaloyl halide, an alkyl or arlysulfonyl halide is used, such as p-toluenesulfonyl chloride. See for example Belgian Pat. Nos. 775,106 and 776,294, Derwent Farmdoc Nos. 33705T and 39011T.

Still another method is by the use of the coupling reagent, dicyclohexylcarbodiimide. See Fieser et al., "Reagents for Organic Synthesis", pp. 231-236, John Wiley and Sons, Inc., New York, (1967). The PG-type compound is contacted with one to ten molar equivalents of the aromatic alcohol in the presence of 2-10 molar equivalents of dicyclohexylcarbodiimide in pyridine as a solvent.

One preferred novel process for the preparation of these esters, however, comprises the steps:

a. forming a mixed anhydride with the TXB-type compound and isobutylchloroformate in the presence of a tertiary amine and b. reacting the anhydride with an appropriate aromatic alcohol.

The mixed anhydride described above is formed readily at temperatures in the range $-40°$ to $+60°$ C., preferably at $-10°$ to $+10°$ C. so that the rate is reasonably fast and yet side reactions are minimized. The isobutylchloroformate reagent is preferably used in excess, for example 1.2 molar equivalents up to 4.0 per mole of the TXB-type compound. The reaction is preferably done in a solvent and for this purpose acetone is preferred, although other relatively nonpolar solvents are used such as acetonitrile, dichloromethane, and chloroform. The reaction is run in the presence of a tertiary amine, for example triethylamine, and the co-formed amine hydrochloride usually crystallizes out, but need not be removed for the next step.

The aromatic alcohol is preferably used in equivalent amounts or in substantial stoichiometric excess to insure that all of the mixed anhydride is converted to ester. Excess aromatic alcohol is separated from the product by methods described herein or known in the art, for example by crystallization. The tertiary amine is not only a basic catalyst for the esterification but also a convenient solvent. Other examples of tertiary amines useful for this purpose include N-methylmorpholine, triethylamine, diisopropylethylamine, and dimethylaniline. Although they are effectively used, 2-methylpyridine and quinoline result in a slow reaction. A highly hindered amine such as 2,6-dimethyllutidine is, for example, not useful because of the slowness of the reaction.

The reaction with the anhydride proceeds smoothly at room temperature (about 20° to 30° C.) and can be followed in the conventional manner with thin layer chromatography (TLC).

The reaction mixture is worked up to yield the ester following methods known in the art, and the product is purified, for example by silica gel chromatography.

Solid esters are converted to a free-flowing crystalline form on crystallization from a variety of solvents, including ethyl acetate, tetrahydrofuran, methanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may also be dried in a current of warm nitrogen or argon, or by warming to about 75° C. Although the crystals are normally pure enough for many applications, they may be recrystallized by the same general techniques to achieve improved purity after each recrystallization.

The compounds of this invention prepared by the processes of this invention, in free acid form, are transformed to pharmacologically acceptable salts by neutralization with appropriate amounts of the corresponding inorganic or organic base, examples of which correspond to the cations and amines listed hereinabove. These transformations are carried out by a variety of procedures known in the art to be generally useful for the preparation of inorganic, i.e., metal or ammonium salts. The choice of procedure depends in part upon the solubility characteristics of the particular salt to be prepared. In the case of the inorganic salts, it is usually suitable to dissolve an acid of this invention in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, an acid of this invention is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing an acid of this invention with the stoichiometric amount of the corresponding quaternary ammonium hydroxide in water solution, followed by evaporation of the water.

DESCRIPTION OF THE PREFERRED EMBODIMENTS

The invention can be more fully understood by the following examples and preparations.

All temperatures are in degrees centigrade.

IR (infrared) absorption spectra are recorded on a Perkin-Elmer Model 421 or 137 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEC model 21-110B Double Focusing High Resolution Mass Spectrometer on an LKB Model 9000 Gas-chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-cyclohexane-water (90:20:50:100) as modified from M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

PREPARATION 1

5α-Hydroxy-2-carboxaldehyde-1α-cyclopent-2-eneacetic acid γ-lactone (Formula XXII).

Refer to Chart A.

A mixture of 136 g. of Florisil and 13.6 ml. of water is shaken until the mixture becomes homogeneous. Thereafter, this mixture is purged with nitrogen, removing any residual oxygen. Thereafter, a solution of 13.6 g. of 3α,5α-dihydroxy-2β-carboxaldehyde-1α-cyclopentaneacetic acid, γ-lactone, benzoate (Formula XXI) in 240 ml. of ethyl acetate is added to the nitrogen purged mixture. This second mixture is then allowed to stand for 12 hr. at ambient temperature and thereafter transferred to a wet-packed column of 400 g. of Florisil and ethyl acetate. Eluting with ethyl acetate, fractions shown to contain pure formula XXII product are combined and concentrated under reduced pressure to yield 5.6 g. of title product. The melting point is 72° to 73.5°

C. Silica gel TLC $R_f$ is 0.69 in ethyl acetate. Characteristic NMR absorptions are observed at 2.5–3.2, 3.5–4.0, 5.1–5.3, 6.8–7.0, and 9.8 $\delta$.

PREPARATION 2

5α-Hydroxy-2-hydroxymethyl-1α-cyclopent-2-eneacetic acid γ-lactone. (Formula XXIII).

Refer to Chart A.

To the solution of 15.6 g. of the reaction product of Preparation 1, 65 ml. of methylene chloride, and 65 ml. of methanol at −15° C. is added with stirring, in small portions, sodium borohydride powder (2.5 g.). The addition proceeds over a period of about 5 min. The mixture is then stirred at about 0° C. for 5 min. at which time 3.8 ml. of acetic acid is cautiously added, with evolution of hydrogen gas. The resulting mixture is then concentrated under reduced pressure. Brine is added to the residue thusly produced and the resulting mixture is extracted with ethyl acetate. The organic extract is then washed with brine containing sodium bicarbonte, dried over magnesium sulfate, and concentrated under reduced pressure to afford 3.2 g. of essentially pure formula XXIII title product. The aqueous layers obtained above are then extracted with 200 ml. of tetrahydrofuran. The organic extract is then dried and concentrated under reduced pressure to afford an additional 2.7 g. of essentially pure formula XXIII product, thereby obtaining a total yield of 5.9 g. Silica gel TLC $R_f$ is 0.42 in ethyl acetate. NMR absorptions are observed at 2.5–2.8, 3.2–3.7, 4.15, 5.0–5.3, and 5.62 $\delta$.

PREPARATION 3

5α-Hydroxy-2-(p-phenylbenzoyloxymethyl)-1α-cyclopent-2-eneacetic acid γ-lactone (Formula XXIV: $R_{31}$ is p-phenylbenzoyl).

Refer to Chart A.

To a solution of 15.4 g. of the reaction product of Preparation 2, 75 ml. of dry tetrahydrofuran, and 75 ml. of dry pyridine at 0° C. is added over a 2 min. period 22 g. of p-phenylbenzoyl chloride with stirring. Thereafter the mixture is cooled in an ice methanol bath, maintaining the reaction temperature below 10° C. When the exothermic reaction has ceased, the cooling-bath is removed and the mixture is stirred at about ambient temperature for 30 min. Thereafter, additional 1.0 g. portions of p-phenylbenzoyl chloride are added at 10 min. intervals until the starting material is completely consumed. Water (5 ml.) is then addd with cooling, thereby destroying excess acid chloride. The mixture is then stirred for an additional 10 min., diluted with 500 ml. of ethyl acetate, and washed with a mixture of 80 ml. of concentrated hydrochloric acid in 800 ml. of an ice-water mixture. Thereafter, the resulting mixture is washed successively with water, dilute potassium bicarbonate, and brine; dried with magnesium sulfate; and concentrated under reduced pressure to yield 38.3 g. of crude product. This crude material is then chromatographed on 2 kg. of silica gel, deactivated by addition of 400 ml. of ethyl acetate. Elution with 4 l. of 1:1 ethyl acetate in Skellysolve B yields crude title product which is combined and concentrated and thereafter washed with dilute potassium bicarbonate and brine and thereafter dried and concentrated under reduced pressure to yield 32.7 g. of pure product. Melting point is 84°–85° C. Silica gel TLC $R_f$ is 0.58 in a mixture of ethyl acetate and hexane (1:1). NMR absorptions are observed at 2.6–2.85, 2.34–3.8, 4.89, 5.0–5.3, 5.83, and 7.38–8.2 $\delta$. Infrared absorptions are observed at 745, 1100, 1175, 1190, 1270, 1280, 1610, 1720, and 1775 cm$^{-1}$. The mass spectrum shows a parent peak 334.1219 and other peaks at 152, 153, 181, and 198.

EXAMPLE 1

2α,3α,5α-Trihydroxy-2β-(p-phenylbenzoyloxymethyl)-1α-cyclopentaneacetic acid 5γ-lactone and its 2β,3β-dihydroxy epimer (Formula XXV: $R_{31}$ is p-phenylbenzoyl).

Refer to Chart A.

To a solution of 32.7 g. of the reaction product of Preparation 3, 300 ml. of acetone, and 40 ml. of water is added a solution of 500 mg. of osmium tetroxide in 25 ml. t-butanol. Thereafter there is added to the resulting solution 17.5 g. of N-methylmorpholine, N-oxide, dihydrate in 25 ml. of water. The mixture thereby produced is stirred at ambient temperature for 1.5 hr. Acetic acid is then added to the mixture and the acetone removed under reduced pressure. To the residue is added 300 ml. of tetrahydrofuran and 1 l. of ethyl acetate and the resulting mixture is washed with (a) a cold mixture of 250 mg. of brine and 15 ml. of concentrated hydrochloric acid, (b) brine, (c) 200 ml. of brine and 25 ml. of saturated aqueous sodium bicarbonate, and (d) brine. The organic layer is then dried over sodium sulfate, and concentrated under reduced pressure. The residue thusly obtained is diluted with 200 ml. of ethyl acetate, cooled, and the resulting precipitate collected to yield 19.13 g. of a crystalline isomer of the title product. (Isomer A; melting point is 166°–167° C.). The filtrate is then concentrated and the residue (16.5 g.) chromatographed on 1 kg. of silica gel, deactivated by addition of 200 ml. of ethyl acetate. Eluting with 2 l. of a mixture of ethyl acetate and hexane (3:1), and thereafter with 2 l. of ethyl acetate, 13.6 g. of a semi solid mixture of isomer A and its 2,3-diepimer (Isomer B) are obtained. Isomer B is obtained in pure form by fractional crystallization of the isomeric mixture from ethyl acetate. Isomer B exhibits melting point of 144°–146° C. For Isomer A infrared absorptions are observed at 745, 1135, 1180, 1215, 1270, 1295, 1610, 1750, and 3500 cm$^{-1}$. The mass spectrum shows a parent peak at 497.1821 and other peaks at 512, 331, 301, 209, 255, 198, 181, 89, 68, and 59. For Isomer B the mass spectrum shows a parent peak at 497.1821 and other peaks at 512, 422, 331, 301, 181, 153, and 145.

EXAMPLE 2

(3S, 4S)-4-hydroxy-6-oxo-3-(p-phenylbenzoyloxyacetyl)-hexanoic acid γ-lactone (Formula XXVI: $R_{31}$ is p-phenylbenzoyl).

Refer to Chart A.

To a solution of 15.5 g. of the reaction product of Example 1 (Isomer A), 300 ml. of methanol, and 22.5 ml. of pyridine at 0° C. is added with stirring and cooling in an ice methanol bath a solution of 14.4 g. of periodic acid (H$_5$IO$_6$) in 40 ml. of water. The aqueous acidic mixture is added at about 20 ml. per minute, so as to maintain the reaction temperature at or below 8° C. A thick precipitate forms quickly and the resulting mixture is stirred vigorously for 15 min. at 0° C. The mixture is then diluted with ethyl acetate, filtered and the precipitate washed with 300 ml. of ethyl acetate. The filtrate and washings are then combined; washed vigorously with (a) 700 ml. of brine, (b) one l. of brine containing 20 ml. of concentrated hydrochloric acid, and (c) 500 ml of brine; dried briefly over magnesium sulfate; and concentrated under reduced pressure to yield a paste, maintaining bath temperature below 35° C. The resulting crude product, being unstable to mild bases (e.g., silica gel) is therefore used without further purification in succeeding examples herein, e.g. Example 3. Silica gel $R_f$ is 0.50 in 7.5 percent methanol in chloroform.

EXAMPLE 3

(3R,4S)-4,6-Dihydroxy-[(1'S)-1-hydroxy-2-(p-phenylbenzoyloxy)ethyl]hexanoic acid 4γ-lactone and its (1'R)-epimer (Formula XXVIII: $R_{31}$ is p-phenylbenzoyl).

Refer to Chart A.

Crude title product of Example 2 (15.5 g.) as obtained from Isomer A is mixed with 150 ml. of methylene chloride, followed by addition of 300 ml. of methanol. This mixture is cooled to about −5° C. and sodium borohydride powder (4 g.) is added in small portions with stirring over about one min. The resulting mixture is then stirred at 0° C. for an additional minute, following the course of the reaction with silica gel thin layer chromatography, developing with ethyl acetate. An intermediate reduction yields the formula XXVII compound: (2RS)-2,4-dihydroxy-2-(p-phenylbenzoyloxymethyl)-3α-tetrahydrofuranacetic acid γ-lactone. Silica gel $R_f$ is 0.78 in ethyl acetate. When the reduction is complete, acetic acid (10 ml.) is cautiously added, causing hydrogen evolution. The resulting mixture is then concentrated under reduced pressure to a volume of about 50 ml. and the residue mixed with 400 ml. of tetrahydrofuran and 600 ml. of ethyl acetate. The resulting mixture is then washed with (a) 500 ml. of brine containing 10 ml. of concentrated hydrochloric acid, (b) 400 ml. of brine containing 15 g. of sodium bicarbonate, and (c) brine. This washed mixture is then dried over magnesium sulfate and concentrated under reduced pressure to yield 13.8 g. of crude title product as a mixture of isomers. This material is then combined with 11.8 g. of an essentially identical isomeric mixture obtained from 15.5 g. of the reaction product of Isomer B of Example 2. The combined isomeric mixture (25.6 g.) is then chromatographed on 2.5 g. of silica gel, deactivated by addition of 375 ml. of acetone and 125 ml. of methylene chloride. The column is then wetted with one l. of a mixture of acetone and methylene chloride (3:7). Crude product is then dissolved in warmed tetrahydrofuran and elution proceeds with mixtures of ethyl acetate and methylene chloride as follows: 8 l. of 3:7 mixture; 4 l. of 2:3 mixture; 4 l. of 1:1 mixture; and 4 l. of 3:2 mixture of volume. Thereupon, 2.34 g. of the (1'R) title product and 13.65 g. of the (1'S) title product are obtained. For the (1'R) isomer, melting point is 159°-160° C. Silica gel $R_f$ is 0.39 in a mixture of acetone and methylene chloride (3:7). Infrared absorptions are observed at 745, 955, 1005, 1045, 1105, 1180, 1285, 1605, 1695, 1760, and 3480 cm.$^{-1}$. The mass spectrum exhibits a parent peak at 499.1984 and other peaks at 313, 303, 255.0845, 213, 198, 181, 103. For there (1'S) epimer, melting point is 135°-136° C. Silica gel $R_f$ is 0.31. Infrared absorptions are observed at 740, 745, 1040, 1115, 1205, 1260, 1270, 1295, 1610, 1710, 1755, 1770, 3320, 3440, and 3540 cm.$^{-1}$. The mass spectrum exhibits a parent peak at 499.1993 and other peaks at 514, 313, 303, 301, 255, 213, 198, and 181 cm.$^{-1}$. For the formula XXVII intermediate, a melting point is observed at 176°-178° C. and characteristic infrared absorptions are observed at 1725, 1780, and 3610 cm.$^{-1}$. The mass spectrum exhibits a parent peak at 440.1655 and other peaks at 425, 313, 229, 198, and 181 cm.$^{-1}$.

EXAMPLE 4

(3S,4S)-4-hydroxy-6-trimethylsilyloxy-3-[(1'S)-2'-(p-phenylbenzoyloxy)-1'-trimethylsilyloxyethyl]hexanoic acid γ-lactone (Formula XXX: $R_{31}$ is p-phenylbenzoyl, and $R_{32}$ is trimethylsilyl).

Refer to Chart A.

To a solution of 21.3 g. of the reaction product of Example 3, 190 ml. of tetrahydrofuran, and 100 ml. of hexamethyldisilizane at ambient temperature is added with stirring 25 ml. of trimethylsilyl chloride. The mixture is then allowed to stand at ambient temperature for about 20 hr. During this period the formula XXIX monosilyl compound is formed: (3R,4S)-4-hydroxy-6-trimethylsilyl-3-[(1'S)-2-(p-phenylbenzoyloxy)-1'-hydroxyethyl]-hexanoic acid γ-lactone. Silica gel TLC $R_f$ is 0.58 in ethyl acetate and hexane (1:1). At the conclusion of this period crude title product is prepared. Silica gel TLC $R_f$ is 0.87 with a mixture of ethyl acetate and hexane (1:1). This mixture containing crude title product is then concentrated to a volume of about 100 ml. under reduced pressure and the residue diluted with 250 ml. of dry benzene. This benzene containing mixture is then filtered and the filtrate washed with benzene. The filtrate and washings are then combined and concentrated under reduced pressure and the residue diluted with 200 ml. of xylene and again concentrated under reduced pressure to yield 29.6 g. of pure title product.

EXAMPLE 5

4α,6-Dihydroxy-2γ-(p-phenylbenzoyloxymethyl)-3α-tetrahydropyranacetic acid γ-lactone (Formula XXXII: $R_{31}$ is p-phenylbenzoyl).

Refer to Chart A.

To a solution of 100 ml. of dry methylene chloride and 6.22 ml. of pyridine at 15° C. is added with stirring 3.9 g. of dried chromium trioxide. This mixture is then stirred at 20°-23° C. for 30 min. and thereafter cooled to 15° C. To this cooled mixture is added a solution of 2.3 g. of the reaction product of Example 4 in 15 ml. of methylene chloride. The resulting mixture is then stirred at ambient temperature for 30 min. Benzene (25 ml.) and 3 g. of Celite are added to the mixture. This resulting mixture is then filtered through a bed of Celite and acid-washed silica gel. Resulting solids are washed with ethyl acetate and the filtrate and washings are combined and concentrated under reduced pressure (at about 25° C.) to a residue which is mixed with ethyl acetate and filtered by the method described above. This second filtrate and ethyl acetate washings are then combined and concentrated under reduced pressure at about 25° C. Accordingly, there is prepared crude formula XXXI compound: (3S,4S)-4-hydroxy-6-oxo-3-[(1'S)-2'-(p-phenylbenzoyloxy)-1'-trimethylsilyloxyethyl] hexanoic acid γ-lactone.

The residue of this crude formula XXXI compound is then dissolved in 25 ml. of tetrahydrofuran, 10 ml. of water, and 5 ml. of acetic acid. The resulting mixture is stirred at ambient temperature for one hr. and the resulting mixture shaken with 75 ml. of ethyl acetate and brine containing excess sodium bicarbonate. The resulting organic layer is then washed with brine, dried over magnesium sulfate, and concentrated under reduced pressure. The residue is then chromatographed on 200 g. of silica gel, deactivated by addition of 40 ml. of ethyl acetate. The column is eluted with ethyl acetate and yields 0.55 g. of crude product which on trituration with ethyl acetate yields 250 mg. of pure title product. Melting point is 172°–174° C. The product recrystallized from ethyl acetate exhibits a melting point of 176°–177.5° C. Silica gel TLC $R_f$ is 0.52 in ethyl acetate and hexane (3:1). The mass spectrum exhibits a parent peak at 440.1633 and other peaks at 425, 284, 283, 271, 255, 243, 230, 198, and 181.

EXAMPLE 6

4α-Hydroxy-6β-methoxy-2β-(p-phenylbenzoyloxymethyl)-3α-tetrahydropyranacetic acid γ-lactone and its 6α-methoxy epimer. (Formula XXXIII, XXXIV, or XXXVa and XXXVb: $R_{31}$ is p-phenylbenzoyl and $R_{33}$ is methyl).

Refer to Chart A.

To a mixture of 500 ml. of dry methylene chloride and 31.1 ml. of pyridine at 15° C. is added with stirring 19.5 ml. of dry chromium trioxide over a period of about 30 seconds. The resulting mixture is then stirred at ambient temperature for 30 min. and thereafter cooled to 10° C. Celite (5 g.) is added, followed by the immediate addition of a solution of 11.9 g. of the reaction product of Example 4, in 40 ml. of dry methylene chloride. The resulting mixture is then stirred at 25° C. for 30 min. and thereafter filtered through a bed of 40 g. of Celite and 80 g. of acid-washed silica gel, moistened with methylene chloride. The filtrate is washed with one l. of diethyl ether and the filtrate and washings are combined and washed quickly with a mixture of 20 ml. of concentrated hydrochloric acid, 200 g. of ice and 250 ml. of brine, and finally with 500 ml. of brine. The washed mixture is then dried over magnesium sulfate and concentrated under reduced pressure, maintaining a bath temperature below 30° C. Accordingly, as in Example 5, crude formula XXXI product is obtained.

The residue of this crude formula XXXI product is then immediately mixed with 150 ml. of ice cold 0.25 N methanolic hydrogen chloride prepared by cautious addition of 4.45 ml. of freshly distilled acetyl chloride to anhydrous methanol and diluting the mixture to a volume of 250 ml. by further addition of methanol. The resulting mixture is then stirred at room temperature for 18 hr. and thereafter diluted with 750 ml. of ethyl acetate. The resulting solution is then washed with a cold mixture of 750 ml. of brine, 200 ml. of water and 7.5 g. of sodium bicarbonate, followed by a further brine wash. The organic phase is then dried over magnesium sulfate and concentrated under reduced pressure to yield 10.3 g. of a residue. This residue is then chromatographed on one kg. of silica gel, deactivated by addition of 200 ml. of ethyl acetate. The residue, diluted in a mixture of Skellysolve B and ethyl acetate (1:1) with addition of sufficient methylene chloride to effect a homogeneous solution, is then applied to the column and the column is eluted with 6 l. of a one to one mixture of ethyl acetate and Skellysolve B followed by 2 l. of ethyl acetate. There is thereby obtained 910 mg. of the title product (formula XXXVa) and 4.03 g. of its 6α-methoxy epimer (formula XXXVb). For the 6β-methoxy epimer silica gel TLC $R_f$ is 0.49 in a mixture of ethyl acetate and hexane (1:1). A characteristic NMR absorption is observed at 3.49δ. For the 6α-methoxy epimer m.p. is 149.5°–150° C. on crystallization from methylene chloride and methanol. Silica gel TLC $R_f$ is 0.36 in ethyl acetate and hexane (1:1). A characteristic NMR absorption is observed at 3.38 δ. Infrared absorptions are observed at 705, 755, 1050, 1105, 1115, 1185, 1280, 1610, 1705, and 1755 cm.$^{-1}$. The mass spectrum exhibits a parent peak at 482.1411 and other peaks at 367, 351, 240, 198, 181, 171, and 153.

EXAMPLE 7

3α-Hydroxy-6-oxo-2β-benzyloxymethyl-3α-tetrahydropyranacetic acid γ-lactone (Formula XLIII: $R_{34}$ is benzyl).

Refer to Chart B.

A. A solution of 30.2 g. of 3α,5α-dihydroxy-2β-benzyloxymethyl-1α-cyclopentaneacetic acid γ-lactone is dissolved in 500 ml. of acetone and the solution cooled to less than 5° C. To this cooled solution is added dropwise, with stirring, 15 ml. of a 2.5 M solution of Jones reagent over a period of 10–15 min. The reaction is stirred for an additional 30 min. and then poured into one l. of dichloromethane and 2 l. of water. The aqueous layer is then separated and extracted with dichloromethane. The combined dichloromethane solutions are then dried over sodium sulfate and concentrated under reduced pressure to yield 30.7 g. of crude formula XLII compound: 3α-hydroxy-5-oxo-2β-benzyloxymethyl-1α-cyclopentaneacetic aicd γ-lactone.

B. The crude reaction product of part A (30.7 g.), an oil, is dissolved in 200 ml. of dichloromethane, and this solution is treated with 40 g. of (0.198 M)m-chloroperbenzoic acid. After stirring for 88 hr. at 25° C., the resulting mixture is diluted with dichloromethane and then extracted with aqueous sodium thiosulfate ($Na_2S_2O_3$), about one l., and with aqueous sodium bicarbonate, about 600 ml. The dichloromethane layer is then dried over sodium sulfate and concentrated under reduced pressure yielding 28 g. of an oil. This oil is then crystallized from ethyl acetate yielding 14.85 g. in a first crop of crystals (melting point 108°–111° C.) and 3.97 g. of a second crop of crystals (melting point 105°–108° C.) These crystals represent pure title product. NMR absorptions are observed at 2.2–3.4, 3.68, 4.2–4.15, and 7.28 δ. Infrared absorptions are observed at 2900, 2850, 1770, 1750, 1460, 1450, 1370, 1260, 1250, 1190, 1040, and 740 cm.$^{-1}$. Silica gel TLC $R_f$ is 0.58 in ethyl acetate and benzene (1:1).

EXAMPLE 8

4,5-Didehydro-6-oxo-2β-benzyloxymethyl-3α-tetrahydropyranacetic acid (Formula XLIV: $R_{34}$ is benzyl).

Refer to Chart B.

The reaction product of Example 7 (18.8 g.) is suspended in 200 ml. of benzene and the resulting mixture treated dropwise with 11.4 g. of 1,5-diazobicyclo[5.4.0]-undec-5-ene (DBU). After stirring 10 min., the reaction is diluted with ethyl acetate and the resulting solution extracted with aqueous 1.0 N hydrochloric acid. The aqueous layer is then separated and extracted twice with additional ethyl acetate. The combined ethyl acetate solutions are then dried over magnesium sulfate and concentrated under reduced pressure yielding 19.2 g. of an oil which on standing yields a waxy solid. Melting point 65°–70° C. This crude title product is then used directly in succeeding examples, e.g., Example 9, without further purification. NMR absorptions are observed at 2.4–2.7, 2.7–3.5, 3.68, 4.3–4.7, 5.97, and 6.80 δ. Silica gel TLC $R_f$ is 0.50 in ethyl acetate in Skellysolve B (1:1).

EXAMPLE 9

4,5-Didehydro-6-hydroxy-2β-benzyloxymethyl-3α-tetrahydroranacetic acid (Formula XLV: $R_{34}$ is benzyl).

Refer to Chart B.

The reaction product of Example 8 (19.2 g.) is dissolved in 400 ml. of dry tetrahydrofuran and the resulting solution treated dropwise at −78° C. for 2 hr. with a solution of 24 ml. of diisobutylaluminum hydride in 250 ml. of toluene. The resulting mixture is then treated dropwise at −78° C. with 100 ml. of a 1.0 N hydrochloric acid solution. The reaction mixture is then warmed to 25° C. and poured into one l. of ethyl acetate. The aqueous layer is then acidified with hydrochloric acid to pH one and separated and extracted twice with ethyl acetate. The combined ethyl acetate solutions are then dried over magnesium sulfate and concentrated under reduced pressure yielding 20.4 g. of crude title product as an oil. This crude product is used without further purification in succeeding examples herein. e.g. Example 10. NMR absorptions are observed at 2.2–3.1, 3.2–4.1, 4.4–4.6, 4.7–5.3, 5.8–6.4, and 7.3 δ. Silica gel TLC $R_f$ is 0.43 in ethyl acetate and Skellysolve B (1:1).

EXAMPLE 10

(3R)-6,6-Dimethoxy-4,5-didehydro-3-(2′-benzyloxy-1′-hydroxyethyl)hexanoic acid γ-lactone (Formula XLVIII: 70 with 100 ml. of a 1.0 N hydrochloric acid solution. The reaction mixture is then warmed to 25° C. and poured into one l. of ethyl acetate. The aqueous layer is then acidified with hydrochloric acid to pH one and separated and extracted twice ethyl acetate. The combined ethyl acetate solutions are then dried over magnesium sulfate and concentrated under reduced pressure yielding 20.4 g. of crude title product as an oil. This crude product is used without further purification in succeeding examples herein. e.g. Example 10. NMR absorptions are observed in 2.2–3.1, 3.2–4.1, 4.4–4.6, 4.7–5.3, 5.8–6.4, and 7.3 δ. Silica gel TLC $R_f$ is 0.43 in ethyl acetate and Skellysolve B (1:1).

EXAMPLE 10

(3R)-6,6-Dimethoxy-4,5-didehydro-3-(2′-benzyloxy-1′-hydroxyethyl)hexanoic acid γ-lactone (Formula XLVIII: $R_{33}$ is methyl and $R_{34}$ is benzyl) and 6α-methoxy-4,5-didehydro-2β-benzyloxymethyl-3α-tetrahydropyranacetic acid, methyl ester (Formula L: $R_{33}$ is methyl and $R_{34}$ is benzyl) or its 6β-methoxy-epimer.

Refer to Chart B.

A. Crude reaction product of Example 9 (20.4 g.) is dissolved in diethyl ether and the resulting solution treated with ethereal diazomethane until the methane color persists. This solution is the concentrated under reduced pressure, yielding the formula XLVI compound: 4,5-didehydro-6-hyroxy-2-benzyloxymethyl-3α-tetrahydropyranacetic acid, methyl ester which on standing lactonizes to 4,5-didehydro-6α-hydroxy-2β-benzyloxymethyl-3β-tetrahydrofuranacetic acid, methyl ester, ε-lactone.

B. The crude residue from part A (either in methyl ester of lactone form or as a mixture thereof) is dissolved in 200 ml. of dry methanol. This solution is treated with 30 ml. of trimethylorthoformate and 5 ml. of 2N hydrogen chloride gas in dry diethyl ether. After stirring for 2.5 hr. at 25° C. the reaction mixture is then treated with 2 ml. of pyridine and concentrated under reduced pressure. The residue is then dissolved in ethyl acetate and extracted with a 5 percent aqueous sodium bicarbonate solution. After drying over magnesium sulfate, the ethyl acetate containing solution is then concentrated under reduced pressure yielding 19.5 g. of an oil, crude title product. This oil is then chromatographed on 1.2 kg. of silica gel, eluting with mixtures of ethyl acetate and Skellysolve B: 3 l. of a 3:7 mixture, 2 l. of a 9:11 mixture; 3 l. of 3:1 mixture, and 2 l. of 3:1 mixture. Accordingly, there is obtained 3.2 g. of the lactone title product XLVIII, 7.7 g. of the 6α-methoxy title product L, and 0.84 g. of the 6β-methoxy title product L. For the lactone title product LXVIII, NMR absorptions are observed at 2.3–2.8, 3.26, 3.62, 4.50, 4.4–4.8, 5.3–6.2, and 7.31 δ. Infrared absorptions are observed at 2900, 1740, 1450, 1360, 1165, 1130, 1070, 1045, and 740 cm.$^{-1}$. Silica gel TLC $R_f$ is 0.29 in ethyl acetate and Skellysolve B (2:3). The 6β-methoxy title product exhibits NMR absorptions at 1.8–3.2, 3.42, 3.65, 3.6–4.0, 4.60, 4.90, 5.6–6.1, and 7.37 δ. Infrared absorptions are observed at 2850, 1740, 1450, 1430, 1360, 1225, 1185, 1025, and 960 cm.$^{-1}$. Silica gel TLC $R_f$ is 0.60 in ethyl acetate and Skellysolve B (2:3) and 0.48 in ethyl acetate and Skellysolve B (3:7). For the 6α-methoxy title product NMR absorptions are observed at 2.03–3.0, 3.43, 3.65, 3.5–4.1, 4.56, 4.90, 5.6–6.15, and 7.33 δ. Silica gel TLC $R_f$ is 0.63 and ethyl acetate in Skellysolve B (2:3) and 0.53 in ethyl acetate and Skellysolve B (3:7).

EXAMPLE 11

6α-Methoxy-5α-iodo-4α-hydroxy-2β-benzyloxymethyl-3α-tetrahydropyranacetic acid γ-lacetone (formula LI: $R_{33}$ is methyl and $R_{34}$ is benzyl).

Refer to Chart B.

The 6α-methoxy reaction product of Example 10 (7.2 g.) is dissolved in 120 ml. of tetrahydrofuran. This solution is then treated with 235 ml. of a 1.0 N aqueous sodium hydroxide solution and the resulting 2 phase system is stirred at 25° C. for 2.5 hr. Solid carbon dioxide is then added until a pH of 10 is obtained. The reaction mixture is then concentrated to about two-thirds of the original volume under reduced pressure, thereby removing the tetrahydrofuran. Thereafter, 10.1 g. of potassium iodine and 15.9 g. of molecular iodine are added to the aqueous residue. The reaction mixture is then stirred for 20 hr. at 25° C. and then poured into dichloromethane. Solid sodium thiosulfate is added and the resulting mixture stirred until the dark iodine color has faded. The aqueous layer is then separated and extracted twice with dichloromethane and the combined organic extracts are then dried over sodium sulfate and concentrated under reduced pressure yielding 8.92 g. of a crystalline product. Recrystallization from ethyl acetate yields 5.48 g. of pure title product as colorless crystals. Melting point is 126°–127° C. NMR absorptions are observed at 2.2 –3.2, 3.38, 3.4–4.0, 4.1–4.4, 4.5–5.3, and 7.32 δ. Infrared absorptions are observed at 2900, 1780, 1500, 1450, 1360, 1260, 970, 840, and 780 cm.$^{-1}$ Silica gel TLC $R_f$ is 0.55 is ethyl acetate and Skellysolve B (2:3).

EXAMPLE 12

6α-Methoxy-4α-hydroxy-2β-benzyloxymethyl-3α-tetrahydrofuranacetic acid γ-lactone (Formula LII: $R_{33}$ is methyl and $R_{34}$ is benzyl).

Refer to Chart B.

The crystalline reaction product of Example 11 (7.51 g.) is dissolved in 90 ml. of dry glyme and 90 ml. of dry ethanol. (See E. J. Corey, et al., Journal of Organic Chemistry 40, 2554 L (1975)). This solution is then treated with 0.9 ml. of tri-n-butyltin chloride dissolved in 9 ml. of ethanol. The resulting solution is then cooled in an ice bath under an argon atmosphere. The mixture is then irradiated with a 150 watt tungsten lamp. While irradiation is proceeding a solution of 0.98 g. of sodium borohydride in 70 ml. of dry methanol is added over 15 min. Bubbling of the reaction mixture is visible throughout the addition. The reaction mixture is then treated with 115 mg. of oxalic acid. The resulting solution is then poured into dichloromethane and a 5 percent aqueous solution of sodium bicarbonate. The aqueous layer is then separated and extracted with dichloromethane and the organic extracts are then dried over magnesium sulfate and concentrated under reduced pressure. The crude residue thereby obtained is then chromatographed on 500 g. of silica gel, eluting with 20 percent ethyl acetate and dichloromethane. Pure title product is thereby obtained (5.37 g.). Melting point is 80°–81° C. NMR absorptions are observed at 2.1–2.9, 3.32, 3.5–4.0, 4.57, 4.50–5.0, and 7.32 δ. Infrared absorptions are observed at 2875, 1775, 1450, 1420, 1360, 1340, 1320, 1240, 1220, 1160, 1100, 1060, 1020, and 920 cm.$^{-1}$. The mass spectrum exhibits parent peak 292.1314. Silica gel TLC $R_f$ is 0.25 in ethyl acetate and Skellysolve B (2:3) and 0.55 in ethyl acetate and dichloromethane (1:4).

EXAMPLE 13

6α-Methoxy-4α-hydroxy-2β-hydroxymethyl-3α-tetrahydropyranacetic acid 4γ-lactone (Formula LXIII: $R_{33}$ is methyl) or its 6β-methoxy epimer.

Refer to Chart C.

A. Preparation of the 6β-methoxy isomer from the reaction product of Example 6:

To a mixture of 2.0 g. of the 6β-methoxy isomer of the reaction product of Example 6, 25 ml. of anhydrous methanol and 3 ml. of dry tetrahydrofuran under a nitrogen atomsphere is added with stirring 1.0 ml. of a 4.40 N solution of methanolic sodium methoxide. The resulting mixture is then stirred at ambient temperature for 25 min. and thereafter acetic acid is added and the mixture cooled and filtered and the filtrate concentrated under reduced pressure. The residue is then chromatographed on 100 g. of silica gel, deactivated with 15 ml. of acetone and 10 ml. of methylene chloride, eluting with one 1. of acetone and methylene chloride (3:7). Accordingly, there is obtained 0.90 g. of 6β-methoxy title product. Silica gel TLC $R_f$ is 0.48 in acetone and methylene chloride (3:7). The mass spectrum exhibits a parent peak at 202.0852 and other peaks at 201, 185, 171, 142, 113, and 87.

B. Preparation of the 6α-methoxy epimer from the reaction product of Example 6:

A solution of 5.53 g. of the 6α-methoxy reaction product of Example 6 and 30 ml. of methylene chloride are added to 90 ml. of 0.15 N methanolic sodium methoxide solution under a nitrogen atmosphere with stirring. The mixture is then stirred at room temperature for 30 min. and thereafter acidified with acetic acid and concentrated under reduced pressure. The residue is then dissolved in ethyl acetate and the mixture filtered and the filtered solid washed thoroughly with ethyl acetate. The filtrate and washings are then combined and concentrated under reduced pressure and the residue chromatographed on 500 g. of silica gel, deactivated by ddition of 75 ml. of acetone and 50 ml. of methylene chloride. Eluting with mixtures of acetone and methylene chloride (1.25 l. of 3:7 mixture, 1.25 l. of 2:7 mixture, and 1.25 l. of a 1:1 mixture by volume) yields 2.25 g. of 6α-methoxy title product and 100 mg. of the formula LXII compound: 6α-methoxy-4α-hydroxy-2β-hydroxymethyl-tetrahydrofuranacetic acid δ-lactone, which compound is relactonized to title product. For the 6α-methoxy title product, silica gel TLC $R_f$ is 0.42 in acetone and methylene chloride (3:7). A characteristic NMR absorption is observed at 4.80 δ (t, J 3.8) and 3.31 δ. Characteristic infrared absorptions are observed at 1780, 3560, and 3690 cm.$^{-1}$. The mass spectrum exhibits parent peak at 202.0848 and other peaks at 201, 185, 171, 142, 113, and 87.

For the formula LXII δ-lactone silica gel TLC $R_f$ is 0.55 in acetone and methylene chloride (3:7). Characteristic NMR absorptions are observed at 4.90 and 3.37 δ. Characteristic infrared absorptions are observed at 1730 and 3550 cm.$^{-1}$.

C. Preparation of the 6α-methoxy title product from the reaction product of Example 12 by hydrogenolysis:

The reaction product of Example 12 (1.39 g.) is dissolved in 100 ml. of 95 percent ethanol and 100 ml. of absolute ethanol. A 1.5 g. quantity of 5 percent palladium on carbon catalyst is added and the mixture hydrogenated at 3 atmospheres pressure. After 1.5 hr. the reaction mixture is filtered and the filtrate concentrated under reduced pressure. The residue is then dissolved in dichloromethane, dried over sodium sulfate, and concentrated under reduced pressure to yield 1.03 g. of pure 6α-methoxy title product as a colorless oil, essentially identical to the reaction product of Part B. NMR absorptions are observed at 2.0–3.1, 3.34, 3.4–3.9, and 4.5–5.0 δ. Infrared absorptions are observed at 3500, 2900, 1775, 1420, 1340, 1320, 1220, 1190, 1160, 1130, 1105, 1060, 1010, 980, 965, 945, and 920 cm.$^{-1}$. The mass spectrum exhibits an M+—OCH$_3$ peak at 171.0660. Silica gel TLC $R_f$ is 0.49 in acetone and dichloromethane (2:3).

EXAMPLE 14

2β-Carboxaldehyde-4α-hydroxy-6α-methoxy-3α-tetrahydropyranacetic acid γ-lactone (Formula LXIV: $R_{33}$ is methyl).

Refer to Chart C.

A. Oxidation employing the Collins reagent:

Chromium trioxide (4.18 g.) is added in portions to 6.75 ml. of pyridine in 70 ml. of dichloromethane at a temperature of about 20° C. The mixture is then stirred for 2 hr. under an argon atomsphere. To this stirred mixture is there is added rapidly 1.05 g. of the reaction product of Example 13 (6α-methoxy epimer) dissolved in 7 ml. of dichloromethane. After about 25 min. the entire reaction mixture is chromatographed on 100 g. of silica gel, eluting with a mixture of 25 percent acetone in methylene chloride. Evaporating fractions containing pure title product there is obtained 425 mg. of the title aldehyde.

B. Oxidation employing a Moffatt reagent:

The reaction product of Example 13 (101 mg.) is dissolved in 1.5 ml. of dichloromethane and the resulting solution treated with 300 mg. of dicyclohexylcarbodiimide in 1.5 ml. of benzene, 0.5 ml. of dimethyl sulfoxide, and 20 ml. of dichloroacetic acid in 0.5 ml. of benzene. After 20 min. the reaction is treated with 127 mg. of oxalic acid, dissolved in 0.3 l. of methanol. After evolution of carbon dioxide ceases, about 10 min., the reaction is filtered and the filtrate chromatographed on 10 g. of silica gel, eluting with acetone and methylene chloride (1:4). Concentrating fractions containing pure title product under reduced pressure yields the title aldehyde.

EXAMPLE 15

Thromboxane B$_2$, 11α-methyl acetal (Formula LXXV: M$_9$ is

or its 15-epimer.

Refer to Chart D.

A. The entire residue from the reaction product of Example 14, part A (425 mg.) is dissolved in 20 ml. of diethyl ether and the solution treated with 4.8 ml. of 0.5 M 2-oxo-heptylidine-tri-n-butyl phosphorane in diethyl ether. After 20 min., the reaction mixture is evaporated and the residue chromatographed on 80 g. of silica gel. The column is eluted with ethyl acetate in n-hexane (1:1) and fractions containing pure 3α-hydroxy-5α-methoxy-2β-(3-oxo-trans-1-octenyl)-3α-tetrahydrofuranacetic acid γ-lactone, a formula LXXII compound, are combined (524 mg.) NMR absorptions are observed at 0.6–1.9, 1.9–3.0, 3.33, 4.25, 4.5–5.0, 6.4, and 6.80 δ. Infrared absorptions are observed at 2900, 1780, 1670, 1160, 1130, 1070, 1050, and 1025 cm.$^{-1}$. The mass spectrum exhibits parent peak at 296.1589. Silica gel TLC R$_f$ is 0.43 in ethyl acetate and Skellysolve B (1:1).

Alternatively, a solution of 13.09 g. of dimethyl-2-oxoheptyl phosphonate in 30 ml. of dry tetrahydrofuran is added with stirring to a cold solution of 5.98 g. of potassium t-butoxide in 250 ml. of dry tetrahydrofuran under a nitrogen atmosphere. The mixture is then stirred at ambient temperature for about 1.5 hr. and the residue of the reaction product of Example 14 from 3.6 g. of LXIII (α-methoxy isomer) diluted with 70 ml. of methylene chloride is added. This hetereogeneous reaction mixture is then stirred at ambient temperature for 2 hr. at which time 3.15 ml. of acetic acid is added. The resulting mixture is then concentrated under reduced pressure and the residue diluted with ethyl acetate and the mixture washed with acidified (hydrochloric acid) brine, basified (sodium bicarbonate) brine, and then dried over magnesium sulfate and concentrated under reduced pressure. The resulting residue (about 12.7 g.) is then chromatographed on 500 g. of silica gel, deactivated by addition of 100 ml. of ethyl acetate. The column is eluted with ethyl acetate and hexane (1:1), yielding 1.17 g. of 4α-hydroxy-6α-methoxy-2β-(3-oxo-trans-1-octenyl)-3α-tetrahydrofuran acetic acid γ-lactone.

B. To a mixture of 2.18 g. of anhydrous zinc chloride and 15 ml. of 1,2-dimethoxyethane under a nitrogen atmosphere is added with stirring 0.61 g. of sodium borohydride. The resulting mixture is then stirred at ambient temperature for 2 hr. and thereafter cooled to −15° C. A solution of 1.17 g. of the reaction product of part A in 10 ml. of 1,2-dimethoxyethane is then added dropwise over about 2 min. The mixture is then stirred at −15° C. for 2 hr., thereafter at 0° C. for one hr. and finally at ambient temperature for about 1.5 hr. The mixture is then cooled to 0° C. and 4.4 ml. of water is added dropwise, with caution (hydrogen gas evolution). The resulting mixture is then diluted with 75 ml. of ethyl acetate and filtered through Celite. The filtrate is then washed with 30 ml. of brine and the organic layer dried over magnesium sulfate and concentrated under reduced pressure. The resulting residue (1.24 g.) is then chromatographed on 125 g. of silica gel, deactivated by addition of 25 ml. of ethyl acetate. Eluting with 500 ml. of ethyl acetate and hexane (3:1) and 500 ml. of ethyl acetate affords 1.05 g. of 4α-hydroxy-6α-methoxy-2β-[(3RS)-3-hydroxy-trans-1-octenyl]-3α-tetrahydropyranacetic acid γ-lactone (formula LXXIII). Epimeric alcohols are then separated employing silica gel thin layer chromatography, eluting with methanol and chloroform (1:19). Alternatively, the epimeric mixture of alcohols is employed directly in succeeding parts of the present Example. For the epimeric mixture, a characteristic NMR absorption is observed at 3.27 δ. The mass spectrum exhibits a parent peak 370.2194 and other peaks at 369, 345, 329, 327, 323, 229, 267, 257, 241, 199, 185, 173, and 129.

C. To a stirred solution of 1.05 g. of the epimeric mixture of the reaction product of part C in 15 ml. of toluene and 10 ml. of dry tetrahydrofuran at −78° C. under a nitrogen atmosphere is added 15 ml. of a 10 percent solution of diisobutylaluminum hydride in toluene over a 5 min. period. The mixture is stirred for 20 min. and thereafter a solution of 3 ml. of water and 10 ml. of tetrahydrofuran is added cautiously with vigorous stirring. The resulting mixture is allowed to warm to ambient temperature and then filtered through Celite, rinsing with ethyl acetate. The filtrate is then shaken with 30 ml. of brine and the resulting mixture filtered through Celite. The filtrate is then washed with brine, and concentrated under reduced pressure to yield 1.0 g. of 4α-hydroxy-6α-methoxy-2β-[(3RS)-3-hydroxy-trans-1-octenyl]-3α-tetrahydropyran acetic acid γ-lactol, an oil. Silica gel TLC R$_f$ is 0.21 and 0.24 in methanol and chloroform (1:19).

The reaction product of part C is prepared directly from the reaction product of part A as follows:

The reaction product of part A (500 mg.) is dissolved in 10 ml. of tetrahydrofuran and the solution cooled to −78° C. under an argon atmosphere. This stirred solution is then treated over 30 min. with 0.7 ml. of diisobutylaluminum hydride, diluted to 2.8 ml. with toluene. The reaction mixture is then treated dropwise with 2 ml. of water and allowed to warm to ambient temperature. Ethyl acetate in 0.25 N aqueous hydrochloric acid are added to the reaction mixture, and the mixture partitioned between organic and aqueous phases. The organic phase is washed with brine, dried over magnesium sulfate and concentrated under reduced pressure to yield 0.364 g. of a crude oil, the (3RS)-3-hydroxy formula LXXIV compound, as above.

D. A mixture of 1.69 g. of 57 percent sodium hydride in mineral oil and 45 ml. of dry dimethylsulfoxide are stirred slowly under nitrogen at 65°–70° C. for one hr. This solution is then cooled to 15° C. and 8.87 g. of 4-carboxybutyltriphenylphosphonium bromide is added. The resulting orange mixture is then stirred for 30 min. at ambient temperature, cooled to 15° C. and the solution of 1.0 g. of the reaction product of part C in 5 ml. of dimethyl sulfoxide is added. The resulting mixture is then stirred at ambient temperature for 2.5 hr. and is then cooled to 15° C. Water is added with cooling, yielding a solution of about pH 9. This solution is then extracted with diethyl ether to remove netural materials. To the aqueous layer is added a suspension of 10 g. of ammonium chloride in 60 ml. of brine and the resulting mixture extracted with ethyl acetate. The ethyl acetate extract is then washed with brine, dried over magnesium sulfate, and concentrated under reduced pressure. The resulting residue (1.5 g.) is chromatographed on 100 g. of acid-washed silica gel, deactivated by addition of 20 ml. of ethyl acetate. Eluting with one l. of ethyl acetate and hexane (1:1) yield 0.43 g. of 11-deoxy-11α-methoxy-15-epi-Thromboxane $B_2$ as an oil, and 0.32 g. of 11-deoxy-11α-methoxy-Thromboxane $B_2$. For the 15-epi compound silica gel TLC $R_f$ is 0.73 in ethyl acetate and hexane (3:1) containing one percent acetic acid. The mass spectrum exhibits parent peak 585.3449 and other peaks at 569, 568, 529, 439, 425, 416, 355, 334, 314, 280, 199, 173, 159, and 117. For the (15S)-epimer silica gel TLC $R_f$ is 0.62 in ethyl acetate and hexane (3:1) containing more percent acetic acid. The mass spectrum exhibits a parent peak at 585.3437 and other peaks at 569, 568, 529, 439, 199, 173, 169, and 117.

EXAMPLE 16

Thromboxane $B_2$ (Formula LXXVII: $R_1$ is hydrogen).

Refer to Chart D.

A solution of one ml. of 85 percent aqueous phosphoric acid and 10 ml. of water is added with stirring to a solution of 220 mg. of the reaction product of Example 15, the (15S)-epimer in 10 ml. of tetrahydrofuran. The resulting solution is then heated to 40° C. for 6 hr. and sodium chloride is thereafter added to the mixture. The resulting mixture is extracted with ethyl acetate and the ethyl acetate extract washed with brine until the aqueous layer is neutral. The organic phase is then dried over magnesium sulfate and concentrated to a residue. The residue (210 mg.) is then chromatographed on 20 g. of acid-washed silica gel, deactivated by addition of 4 ml. of ethyl acetate. Eluting with 70 ml. of ethyl acetate and hexane (3:1), and 100 ml. of ethyl acetate yields 170 mg. of thromboxane $B_2$. Silica gel TLC $R_f$ is 0.38 in acetic acid and ethyl acetate (1:99). The mass spectrum for the methyl ester, tris TMS derivative exhibits a peak at 585 and other peaks at 529, 510, 495, 439, 429, 256, and 225.

Following the procedure of Examples 1-6, but employing in place of the 2-(phenylphenylbenzoyloxymethyl) starting material of Preparation 3, each of the various correspnding hydroxy hydrogen replacing groups according to $R_{31}$, there are obtained respective products corresponding to those of Examples 1-6. Accordingly, employing 5α-hydroxy-2α-benzoyloxymethyl-1α-cyclopent-2-eneacetic acid γ-lactone, there are obtained the corresponding benzoyloxy-containing compounds as follows:

2α,3α,5α-Trihydroxy-2β-benzoyloxymethyl-1α-cyclopentaneacetic acid 5γ-lactone and its 2β,3β-dihydroxy epimers;

(3S,4S)-4-Hydroxy-6-oxo-3-benzoyloxyacetylhexanoic acid γ-lactone;

(3R,4S)-4,6-Dihydroxy-[(1'S)-1-hydroxy-2-benzoyloxyethyl]-hexanoic acid γ-lactone and its (1'R)-epimer;

(3S,4S)-4-Hydroxy-6-trimethylsilyloxy-3-[(1'S)-2'-benzoyloxy-1'-trimethylsilyloxyethyl]-hexanoic acid γ-lactone;

3α,6-Dihydroxy-2β-benzoyloxymethyl-3α-tetrahydropyranacetic acid γ-lactone; and

4α-Hydroxy-6β-methoxy-2β-benzoyloxymethyl-3α-tetrahydropyranacetic acid γ-lactone and its 6α-methoxy epimer.

Likewise, following the procedure of Examples 1-6, but employing 5α-hydroxy-2-tetrahydropyranyloxymethyl-1α-cyclopent-2-eneacetic acid γ-lactone in place of the starting material of Preparation 3, there are prepared the corresponding tetrahydropyranyloxy-containing compounds, as follows:

2α,3α,5α-Trihydroxy-2β-tetrahydropyranyloxymethyl-1α-cyclopentaneacetic acid 5γ-lactone and its 2β,3β-dihydroxy epimers;

(3S,4S)-4-Hydoroxy-6-oxo-3-tetrahydropyranyloxyacetylhexanoic acid γ-lactone;

(3R,4S)-4,6-Dihydroxy-[(1'S)-1-hydroxy-2-tetrahydropyranyloxyethyl]hexanoic acid 4γ-lactone and its (1'R)-epimers;

(3S,4S)-4-Hydroxy-6-trimethylsilyloxy-3-[(1'S)-2'-tetrahydropyranyloxy-1'-trimethylsilyloxyethyl]hexanoic acid γ-lactone;

3α,6-Dihydroxy-2β-tetrahydropyranyloxyacetic acid γ-lactone; and

4α-Hydroxy-6β-methoxy-2β-tetrahydropyranyloxymethyl-3α-tetrahydropyranacetic acid γ-lactone and its 6α-methoxy epimer.

Further, following the procedure of Examples 1-6, but employing 5α-hydroxy-2-benzyloxymethyl-1α-cyclopent-2-ene-acetic acid γ-lactone in place of the starting material of Preparation 3, there are obtained the corresponding benzyloxy-containing compounds, as follows:

2α,3α,5α-Trihydroxy-2β-benzyloxymethyl-1α-benzyloxymethyl-1α-cyclopentaneacetic acid 5γ-lactone and its 2β,3β-dihydroxy epimers;

(3S,4S)-4-Hydroxy-6-oxo-3-benzyloxyacetyl-hexanoic acid γ-lactone;

(3R,4S)-4,6-Dihydroxy-[(1'S)-1-hydroxy-2-benzyloxyethyl]-hexanoic acid 4γ-lactone and its (1'R)-epimers;

(3S,4S)-4-Hydroxy-6-trimethylsilyloxy-3[(1'S)-2'-benzyloxy-1'-trimethylsilyloxyethyl]hexanoic acid γ-lactone;

3α,6-Dhydroxy-2β-benzyloxyacetic acid γ-lactone; and

4α-Hydroxy-6β-benzyloxymethyl-3α-tetrahydropyranacetic acid γ-lactone and its 6α-methoxy epimer.

Following the procedures of Examples 7-12, but employing in place of the Formula XLI benzyloxyether, each of the various other arylmethyl-containing compounds according to formula XLI wherein $R_{34}$ is not benzyl, there are obtained each of the various $R_{34}$-ethers corresponding to each of the reaction products of Examples 7-12.

Further, following the procedures of Examples 6, 10, 11, and 12, but employing in Example 6 and Example 10 an homologous alkyl reagents to the methyl-containing reagents employed therein, there are obtained each of the various 6α- or 6β-alkoxy products of one to 5 carbon atoms, inclusive, correponding to the 6α- or 6β-methoxy reaction products of these Examples. Further, employing these homologous alkyl reagents in conjunction with each of the various $R_{31}$- or $R_{34}$-containing compounds corresponding to starting material for Examples 6, 10, 11 or 12, there are obtained corresponding products.

Further, following the procedure of Examples 13 and 14, but using the 6α- or 6β-alkoxy reactant of formula LXI, in place of the 6α- or 6β-methoxy starting material of Example 13, there are obtained the corresponding 6α- or 6β-alkoxy products, of one to 5 carbon atoms, inclusive.

Finally, following the procedure of Example 15, but employing in place of the 6α- or 6β-methoxy starting materials therein the various 6α- or 6β- formula LXXI reactants, of one to 5 carbon atoms, inclusive, of Formula LXXI there are obtained the corresponding Thromboxane $B_2$, 11α-alkyl acetals, of one to 5 carbon atoms, inclusive, or their respective 15-epimers. Accordingly, there is obtained Thromboxane $B_2$, 11α-ethyl acetal or its 15-epimer.

Preparation 4

$PGF_{2\alpha}$, methyl ester, 9,15-diacetate (Formula LXXXIV: $R_1$ is methyl and $R_9$ is acetal).

Refer to Chart E.

A. To a solution of $PFG_{2\alpha}$, 11,15-bis(tetrahydropyranylether), methyl ester (0.77 g.) in pyridine (5 ml.) is added acetic anhydride (2 ml.). The mixture is stirred for about 4 hr. under a nitrogen atmosphere and thereafter water (50 ml.) is added and the resulting mixture stirred for an additional one hr. The resulting mixture is then extracted with ethyl acetate and the combined organic extracts are then washed, dried, and concentrated to yield $PGF_{2\alpha}$, 11,15-bis-(tetrahydropyranyl ether), methyl ester, 9-acetate ( a formula LXXXII compound).

B. The reaction product of part A is treated with a mixture of water, tetrahydrofuran, and acetic acid, and thereafter freeze-dried. The residue thusly obtained is then chromatographed on silica gel, yielding pure $PGF_{2\alpha}$, methyl ester, 9-acetate, a formula LXXXIII compound.

C. A solution of 3.28 g. of $PGF_{2\alpha}$, methyl ester, 9-acetate in 82 ml. of pyridine is then cooled to about 0° C. and with stirring 16.4 ml. of acetic anhydride is added. Stirring at 0° C. is then continued for 90 min. and thereafter ice and water are added. The resulting mixture is then partitioned by addition of ethyl acetate and the organic layer thusly obtained is washed with 3N hydrochloric acid, saturated sodium bicarbonate, and brine. The resulting mixture is then dried over sodium sulfate and concentrated under reduced pressure. The residue so obtained is then chromatographed on 400 g. of silica gel eluting with 20 to 100 percent ethyl acetate in Skellysolve B.

Thereby, 0.742 g. of $PGF_{2\alpha}$, methyl ester, 9,15-diacetate are obtained. Silica gel TLC $R_f$ is 0.59 employing the A-IX solvent system.

EXAMPLE 17

$TXB_2$, methyl ester (Formula XCVI: $R_1$ is methyl).

Refer to Chart F.

A. A solution of 800 mg. of $PGF_{2\alpha}$, methyl ester, 9.15-diacetate in 32 ml. of dry benzene is treated with 1.21 g. of lead-tetraacetate (recrystallized from acetic acid and dried under reduced pressure over potassium hydroxide) at 50° C. under a nitrogen atmosphere. Reaction conditions are maintained for about 70 min. The resulting mixture is then filtered through Celite and the filtrate washed with brine. The process of filtration is repeated and the second such filtrate is washed with brine, dried over sodium sulfate, and evaporated under reduced pressure at ambient temperature to yield a crude light yellow oil (900 mg.), (8S,9R,12S)-8-[(1'S)-3'-oxo-1'-hydroxypropyl]-9,12-dihydroxy-5-cis-9-trans-heptadecadienoic acid, methyl ester, 9,12,1'-triacetate, a formula XCII compound. Characteristic infrared absorptions are observed at 2750, 1745, 1370, 1230, 1150, 1050, 1020, and 970 cm.$^{-1}$. NMR absorptions are observed at 9.9, 5.9, 5.0, 3.7, 2.05, and 0.97 δ.

B. The entire crude reaction product from part A is then dissolved in 16 ml. of dry methanol, 2.5 ml. of trimethyl orthoformate, and 175 mg. of pyridine hydrochloride. This mixture is then stirred over a nitrogen atmosphere for about 60 hr. at ambient temperature. Thereafter about 30 ml. of dry benzene is added and the methanol removed by concentration under reduced pressure. The resulting benzene-containing solution is then washed twice with brine, dried over sodium sulfate, and concentrated, yielding a residue of about 950 mg. This residue is then chromatographed on silica gel, eluting with 50 to 75 percent ethyl acetate in hexane. Fractions containing pure (8S,9R,12S)-8-[(1'S)-3'-oxo-1'-hydroxypropyl]-9,12-dihydroxy-5-cis-10-trans-heptadecadienoic acid, methyl ester, 9,12,1'-triacetate, dimethylacetal (436 mg.) are combined, yielding the formula XCIII thromboxane intermediate. Infrared absorptions are observed at 1750, 1175, 1240, 1210, 1130, 1050, 1020, and 975 cm.$^{-1}$. The mass spectrum exhibits peaks at 556, 525, 497, 465, 404, 362, 344, 311, 139, 75, and 43.

C. A solution of 110 mg. of sodium and 10 ml. of dry methanol is prepared under a nitrogen atmosphere and to this mixture is added a solution of 420 mg. of the reaction product of part B and 5 ml. of dry methanol. The resulting mixture is then stirred at ambient temperature for 1.5 hr. and thereafter 0.5 ml. of acetic acid is added, followed by addition of benzene. Thereafter, the methanol is substantially removed by evaporation under reduced pressure. This benzene containing solution is then washed with brine, dried over sodium sulfate, and evaporated to yield 360 mg. of a pale yellow oil. This oil is then chromatographed on silica gel eluting with two percent methanol and ethyl acetate. Fractions containing pure (8S,9R,12S)-7-[(1'S)-3'-oxo-1'-hydroxypropyl]-9,12-dihydroxy-5-cis-10-trans-heptadecadienoic acid methyl ester dimethylacetal (218 mg.) are obtained. Silica gel TLC $R_f$ is 0.19 in the A-IX solvent system. Infrared absorptions are observed at 3350, 1740, 1370, 1310, 1240, 1190, 1125, 1045, and 975 cm.$^{-1}$. The mass spectrum exhibits peaks at 380, 362, 349, 184, 99, and 75.

D. A mixture of 187 mg. of the reaction product of part C under a nitrogen atmosphere is treated with a mixture of 4 ml. of acetic acid, 2 ml. of water, and 1 ml. of tetrahydrofuran for about 4 hr. Thereupon, the resulting mixture is stirred at ambient temperature under vacuum for about one hr. and the mixture then freeze dried and chromatographed on silica gel eluting with one percent methanol and ethyl acetate. There are thereby obtained 49 mg. of 11-deoxy-11α- and 11β-methoxy-TXB-hd 2, methyl ester and 0.44 g. of $TXB_2$, methyl ester. For the 11-methoxy-compounds silica gel TLC $R_f$ is 0.66 in one percent methanol in ethyl acetate. For $TXB_2$ methyl ester silica gel TLC $R_f$ is 0.44 in one percent methanol and ethyl acetate.

E. The reaction product of part A in dry methanol is allowed to stand for several days in the presence of 2N ethereal hydrochloric acid yielding 11-deoxy-11α- and 11β-methoxy-TXB₂ methyl ester.

F. The reaction product of part C (258 mg.) dissolved in 12 ml. of tetrahydrofuran and treated under a nitrogen atmosphere with 10 ml. of water and one ml. of 85 percent phosphoric acid are stirred at ambient temperature for about 35 hr. Thereafter the mixture saturated with sodium chloride and extracted with ethyl acetate. The ethyl acetate extracts are then washed with brine, dried over sodium sulfate, and concentrated to a 232 mg. residue. This residue is then chromatographed on silica gel yielding 59 mg. of 11-deoxy-11α- and 11β-methoxy TXB₂, methyl ester and 110 mg. of TXB₂, methyl ester.

Following the procedure of Example 17, but employing PGF$_{2α}$, methyl ester, 9,15-dibenzoate in place of the 9,15-diacetate starting material, there are obtained the corresponding formula XCII 8,11-dibenzoate, formula XCIII 8,11-dibenzoate, formula XCIII 88,11-dibenzoate, and formula XCIV-XCVI products as in Example 17. Likewise, employing each of the various diacylates according to R₉ in place of the 9,15-diacetate starting material for Example 17, there are obtained the corresponding 8,11-diacylate TXB₂ intermediates of formula XCII and formula XCIII.

EXAMPLE 18 TXB₂ and 11-deoxy-11α- or 11β-methoxy-TXB₂

Refer to Chart F

A. A solution of 300 mg. of the reaction product of part B of Example 17 in 5 ml. of dry methanol under nitrogen is treated at room temperature with 10 ml. of a sodium methoxide solution (120 mg. sodium dissolved in 10 ml. of methanol) for 45 min. Then 6 ml. of water is added and stirring is continued for 135 min. to hydrolyze the methyl ester. A solution of 2.5 ml. of 85 percent phosphoric acid in water is added and some of the methanol is removed at reduced pressure. The aqueous residue is then extracted with ethyl acetate. The extracts are dried over sodium sulfate and evaporated, yielding 260 mg. of the residue: formula XCIV, R₁ is hydrogen and R₃₃ is methyl R$_f$ is 0.17 in the A-IX system. NMR absorptions are observed at 5.45, 4.61, 4.0, 3.38, and 0.96 δ.

B. The 260 mg. residue of part A is dissolved in 12 ml. tetrahydrofuran and treated with 9 ml. of water and 1 ml. of 85 percent phosphoric acid for 4.5 hr. at room temperature as in part F. The reaction mixture is worked up as in part F of Example 17 and chromatographed on silica gel to give 11-deoxy-11α- and 11β-methoxy TXB₂, 50 mg. and TXB₂, 100 mg.

I claim:

1. A thromboxane intermediate of the formula

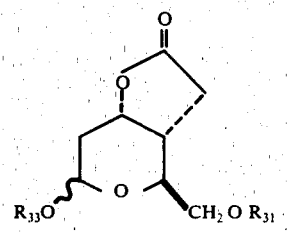

wherein R₃₁ is a hydroxy-hydrogen replacing group selected from the group consisting of R₉, R₁₀, and R₃₄;

wherein R₉ is an acyl protecting group selected from the group consisting of
a. benzoyl;
b. benzoyl substituted with one to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the subtituents does not exceed 10 carbon atoms, with the further proviso that the substituents are the same or different;
c. benzoyl substituted with alkoxycarbonyl of 2 to 5 carbon atoms; inclusive;
d. naphthoyl;
e. naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either side of the fused aromatic rings are other than alkyl and that the total number of carbon atoms in the substituents on either of the fused aromatic rings does not exceed 10 carbon atoms, with the further proviso that the various substituents are the same or different; and
f. alkanoyl of 2 to 12 carbon atoms, inclusive;

wherein R₁₀ is a blocking group selected from the group consisting of
a. tetrahydropyranyl;
b. tetrahydrofuranyl; and
c. a group of the formula

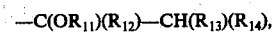

—C(OR₁₁)(R₁₂)—CH(R₁₃)(R₁₄), wherein R₁₁ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein R₁₂ and R₁₃ are alkyl of one to 4 carbon atoms, inclusive, phenyl, phenyl substituted with one, 2, or 3 alkyl or one to 4 carbon atoms, inclusive, or when R₁₂ and R₁₃ are taken together —(CH₂)₂— or —(CH₂)$_b$—O—(CH₂)$_c$, wherein a is 3,4, or 5, or b is one, 2, or 3, and c is one, 2, or 3, with the proviso that b plus c is 2,3, or 4, with the further proviso that R₁₂ and R₁₃ may be the same or different, and wherein R₁₄ is hydrogen or phenyl;

wherein R₃₄ is an arylmethyl hydroxy-hydrogen replacing group selected from the group consisting of
a. benzyl,
b. benzyl substituted by one to five alkyl of one to four carbon atoms, inclusive, chloro, bromo, iodo, fluoro, nitro, phenylalkyl of 7 to 12 carbon atoms, inclusive, with the further proviso that the various substituents are the same or different,
c. benzhydryl,
d. benzhydryl substituted by one to ten alkyl of one to four carbon atoms, inclusive, chloro, bromo, iodo, fluoro, nitro, phenylalkyl of 7 to 12 carbon atoms, inclusive, with the further proviso that the various substituents are the same or different,
e. trityl, and
f. trityl substituted by one to 15 alkyl of one to four carbon atoms, inclusive, chloro, bromo, iodo, fluoro, nitro, phenylalkyl of 7 to 12 carbon atoms, inclusive, with the further proviso that the various substituents are the same or different; and wherein $R_{33}$ is alkyl of one to 5 carbon atoms, inclusive.

2. 4α-Hydroxy-6α- or 6β-methoxy-2β-benzoyoxymethyl-3α-tetrahydropyranylacetic acid γ-lactone, thromboxane intermediates according to claim 1.

3. 4α-Hydroxy-6α- or 6β-methoxy-2β-tetrahydropyranyloxymethyl-3α-tetrahydropyranylacetic acid γ-lactone, thromboxane intermediates according to claim 1.

* * * * *

UNITED STATES PATENT OFFICE
CERTIFICATE OF CORRECTION

Patent No. 4,048,194     Dated September 13, 1977

Inventor(s) Norman A. Nelson

It is certified that error appears in the above-identified patent and that said Letters Patent are hereby corrected as shown below:

Column 2, lines 45-50, that portion of the formula reading

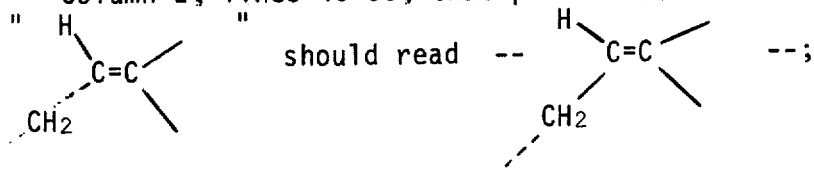

Column 13, lines 20-22, that portion of the formula reading

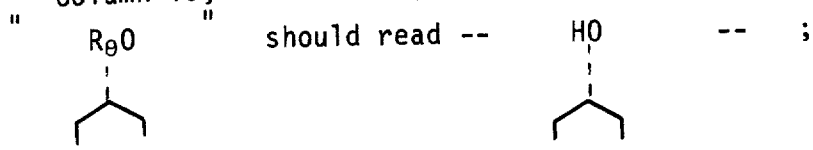

Column 16, line 19, "-SI-$(G_1)_3$" should read -- -Si-$(G_1)_3$ --; line 64, "includive," should read -- inclusive, --;
Column 18, line 34, "chromatographi" should read -- chromatographic --; lines 44-45, "formul" should read -- formula --
Column 19, line 3, "formul" should read -- formula --;
Column 21, line 4, "between -10° and -10° C." should read -- between -10° and +10° C. --;

UNITED STATES PATENT OFFICE
CERTIFICATE OF CORRECTION

Patent No. 4,048,194  Dated September 13, 1977

Inventor(s) Norman A. Nelson

It is certified that error appears in the above-identified patent and that said Letters Patent are hereby corrected as shown below:

Column 26, line 46, "The PG-type" should read -- The TXB-type --;

Column 35, lines 27-42 should be omitted;
Column 36, line 11, "3 1. of 3:1 mixture" should read -- 3 1. of 3:2 mixture --; line 19, "2900, 1740, 1450" should read -- 2900, 1780, 1740, 1450 --;
Column 37, lines 1/2, "tetrahydrofuranacetic" should read -- tetrahydropyranacetic --, line 10, "2554 L (1975))." should read -- 2554 (1975)). --;
Column 39, line 61, "tetrahydrofuran" should read -- tetrahydropyran --;
Column 42, lines 37/38, "2β-benzyloxymethyl-1α-benzyloxymethyl-1α" should read -- 2β-benzyloxymethyl-1α --; line 49, "4α-Hydroxy-6β-benzyloxymethyl-" should read -- 4α-Hydroxy-6β-methoxy-2β-benzyloxymethyl --;
Column 44, line 62, "-TXB-hd 2," should read -- $TXB_2$, --;
Column 45, lines 20/21, "XCIII 8,11-dibenzoate, formula XCIII 88, 11-dibenzoate," should read -- XCIII 8,11-dibenzoate, --;
Column 46, line 41, "alkyl or one" should read -- alkyl of one --; line 43, "together-$(CH_2)_2$-" should read -- together -$(CH_2)a$- --.

Signed and Sealed this

Twenty-seventh Day of June 1978

[SEAL]

Attest:

RUTH C. MASON
Attesting Officer

DONALD W. BANNER
Commissioner of Patents and Trademarks

UNITED STATES PATENT OFFICE
CERTIFICATE OF CORRECTION

Patent No. 4,048,194    Dated 13 September 1977

Inventor(s) Norman A. Nelson

It is certified that error appears in the above-identified patent and that said Letters Patent are hereby corrected as shown below:

Column 9, lines 30-33, that portion of the formula reading

Column 12, lines 15-20, that portion of the formula reading

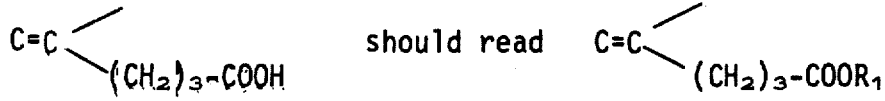

Column 23, line 15, "$(R_{15}O)_2$" should read --

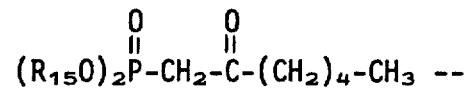

Column 32, line 37, "$4\alpha,6$-Dihydroxy-$2\gamma$-" should read -- $4\alpha,6$-Dihydroxy-$2\beta$- --;

Column 35, lines 5-6, "tetrahydroranacetic" should read -- tetrahydropyranacetic --.

Signed and Sealed this

Twenty-fourth Day of March 1981

[SEAL]

Attest:

RENE D. TEGTMEYER

Attesting Officer    Acting Commissioner of Patents and Trademark